(12) United States Patent
Miyake

(10) Patent No.: US 8,460,219 B2
(45) Date of Patent: Jun. 11, 2013

(54) WALKING AID SYSTEM

(75) Inventor: Yoshihiro Miyake, Yokohama (JP)

(73) Assignee: Tokyo Institute of Technology, Tokyo (JP)

( * ) Notice: Subject to any disclaimer, the term of this patent is extended or adjusted under 35 U.S.C. 154(b) by 1063 days.

(21) Appl. No.: 11/576,645

(22) PCT Filed: Oct. 5, 2005

(86) PCT No.: PCT/JP2005/018730
§ 371 (c)(1),
(2), (4) Date: Aug. 21, 2008

(87) PCT Pub. No.: WO2006/038712
PCT Pub. Date: Apr. 13, 2006

(65) Prior Publication Data
US 2011/0166488 A1    Jul. 7, 2011

(30) Foreign Application Priority Data

Oct. 5, 2004   (JP) .................................. 2004-293136

(51) Int. Cl.
*A61B 5/00*    (2006.01)

(52) U.S. Cl.
USPC ....................................................... 600/595

(58) Field of Classification Search
USPC ........ 482/3, 9; 600/595; 601/33, 34; 702/150
See application file for complete search history.

(56) References Cited

U.S. PATENT DOCUMENTS

| | | | | |
|---|---|---|---|---|
| 4,776,323 A | * | 10/1988 | Spector | 601/23 |
| 5,963,891 A | * | 10/1999 | Walker et al. | 702/150 |
| 6,734,834 B1 | | 5/2004 | Baram | |
| 6,837,827 B1 | * | 1/2005 | Lee et al. | 482/8 |
| 2003/0088294 A1 | | 5/2003 | Gesotti | |

FOREIGN PATENT DOCUMENTS

| | | |
|---|---|---|
| EP | 0 627 238 A2 | 12/1994 |
| EP | 627238 A2 * | 12/1994 |
| JP | 6-273546 A | 9/1994 |
| JP | 2001-101547 A | 4/2001 |
| JP | 2002-306628 A | 10/2002 |
| JP | 2004-73649 A | 3/2004 |
| JP | 2004-89355 A | 3/2004 |
| JP | 2005-227909 A | 8/2005 |

OTHER PUBLICATIONS

Japanese Office Action dated Oct. 20, 2009, issued in corresponding Japanese Patent Application No. 2004-293136.

(Continued)

*Primary Examiner* — Max Hindenburg
(74) *Attorney, Agent, or Firm* — Westerman, Hattori, Daniels & Adrian, LLP

(57) ABSTRACT

An object of the present invention is to realize mutual adaptation for mutual synchronizing in a man-machine system and make it applicable to the site of walking aid. A walking aid system of the present invention comprises: a sensor section (2) for sensing the motion rhythm of a walker, a recording section (33) for recording values of measurements of the motion rhythm sensed with the sensor section 2, a target setting section (34) for setting a target value for the motion rhythm of the walker, a timing generating section (36) for generating a timing signal according to the difference between the measurement and the target value, and a stimulus generating section (4) for generating rhythm stimulus that is recognizable by the walker, according to the timing signal generated with the timing generating section (36).

11 Claims, 17 Drawing Sheets

OTHER PUBLICATIONS

Japanese Office Action dated Nov. 30, 2010, issued in corresponding Japanese Patent Application No. 2004-293136.
International Search Report of PCT/JP2005/018730, date of mailing Feb. 10, 2006.
Takanashi, Hideya et al.;"Co-emergence Robot Walk-Mate and Its Support for Elderly People"; The Society of Instrument and control Engineers, Japan, Jan. 2003, vol. 39, No. 1, pp. 74-81.
Japanese Office Action dated Feb. 23, 2010, issued in corresponding Japanese Patent Application No. 2004-293136.
Japanese Office Action dated Jun. 1, 2010, issued in corresponding Japanese Patent Application No. 2004-293136.
Sagawa, Koichi et al.; "A reduction method of integral error for estimation of 3D walking distance"; Proceedings of the Japan Society of Mechanical Engineers (Information, Intelligence and Precision Equipment Division) Conference; Mar. 22, 2002, vol. 2002, pp. 171-176.
Sagawa, Koichi et al.; "Estimation of 3D distance during indoor and outdoor locomotion"; Proceeding of the Japan Society of Mechanical Engineers Annual Conference; Sep. 20, 2002, vol. 2002, No. 6, pp. 161-162.

* cited by examiner (a) Slow (b) Natural (c) Fast (c) Patient A (d) Patient A with Walk-Mate

WALKING AID SYSTEM

TECHNICAL FIELD

The present invention relates to a walking aid system, and more particularly to the walking aid system for aiding walk motion and rehabilitation for the aged or the physically handicapped.

BACKGROUND ART

Walking aid for the aged and the walk-handicapped is often carried out in the form of cooperation approach between the patient and the physical therapist. One reason for the effectiveness of the above aid method utilizing person to person communication is that walking aid functions matching situations can be created from one minute to the next while the patient and the physical therapist adapt their physical motions to each other through communication. In the musical kinetotherapy for example, the music played by the therapist and the physical motion of the patient are matched each other in rhythm and timing intended for improving physical kinetic function, and its effectiveness is now drawing attention.

As a currently common aid system, one using bio-feedback may be named. This is a system with which the biological signal such as the myoelectric potential that the patient himself cannot perceive is fed back as recognizable sensory information to help the patient consciously control his own motion and acquire motion capability. On the other hand, actually a number of incidents have been reported that, while the effect is seen while the patient is treated with the feedback therapy, continuation of the effect is not confirmed after the treatment.

Along with the development of robotics, an aid system is also proposed to carry out aid with dynamic actuators mounted on the human body. For example, there is a system related to the motor-operated artificial arm and the motor-operated artificial leg that control the motors according to myoelectric potentials. Lately a system serving as a power assist device has been developed that is directly attached to the leg to assist the walking motion. While the above system may be seen as a kind of the above bio-feedback, direct, dynamic operation of the physical motion is its characteristic.

On the other hand, the inventors have already proposed a method of controlling the tempo of motion such as walking using rhythm stimulus synchronized with the physical motion. The method is to sense the motion rhythm of a moving person with a sensor, a pacemaker produces timing according to the difference between the sensed motion rhythm and its target value, and feed it back as a rhythm stimulus through a headphone or the like to the motion tempo of the moving person.

DISCLOSURE OF THE INVENTION

However, the object of the system using the biofeedback is for the patient to unilaterally adapt to the aid system in order to achieve a targeted ideal state, departing broadly from the above-described object of aiding to create motion function through "mutual adaptation" with both sides approaching each other. Further, there have been incidents in which no continuation of effect is recognized. From such a background, particularly in the field of walking aid, a system development capable of assisting creation of mutually adaptive functions has been in need.

Further, these power assist devices are aid systems which orient to the physical motion than to the human communication. Furthermore, there is a problem of increased size and weight since they use dynamic hardware such as electric motor and the like. Furthermore, since dynamic drive components are directly attached to the human body, inherent limitation has been pointed out that the patient is exposed to danger in case of malfunction.

A method using the rhythm stimulus as the pacemaker is expected to be effective in overcoming problems the background technology has. In other words, the system development is considered to be possible that is oriented to human communication and is capable of aiding function creation process. Moreover, since no dynamic hardware is required, it is free from problems of undesirably increased weight and size, and exposure of patients to danger in case of malfunction.

However, the idea of controlling the man-machine system in mutually adaptive manner utilizing the mutual rhythm entrainment depends on an undisclosed control method of nonlinear system proposed thereafter by the inventors (relational system control method) Japanese Patent Laid Open Publication No. 2005-227909 and were made possible by utilizing the method according to the present invention.

As for the evaluation of aid effect, it has heretofore depended on the subjective symptom description by doctors and physical therapists present at the site of aid. In another aspect, motion dynamics analyzing devices on a very large scale such as optical position measurement device and floor reaction force device have been used for research purposes. In other words, evaluation method has been absent between the subjective evaluation on the site of aid and the evaluation for the study purpose. An objective evaluation method has also been sought after, regarding the gait that is an expression of walk.

Therefore, the first object of the present invention is to control the man-machine system in mutually adaptive manner utilizing the mutual rhythm entrainment by combining the method of using the rhythm stimulus as pacemaker with the relational system control method for realizing the mutual adaptation in the man-machine system, both method and technique being proposed by the inventors. Further it is intended to provide a walking aid system for assisting the aged and the physically handicapped in their walking and rehabilitation by developing these techniques from the stage of controlling the tempo of action such as walking by rhythm stimulus. For the above, the following problems remain to be solved.

First, there is a problem of developing walk motion measurement and rhythm stimulus method applicable to various types of walk disability aid and rehabilitation. For example, methods of motion measurement and stimulus presentation based on individual disability such as hemiplegic walk caused by cerebral blood vessel disturbance, and accelerated walk or cowering caused by Parkinson's disease are required.

Another problem is that a method of evaluating how walking motion is improved by walking aid and rehabilitation must be developed. In other words, a problem remains how to evaluate the improvement effect of walking aid including the case in which the method of using the rhythm stimulus as pacemaker and the relational system control method of realizing mutual adaptation in the man-machine system are applied to walking aid. Further there is no objective evaluation method for the gait of the walker, so that a problem how to evaluate it remains.

From the above, an object of the present invention is to realize mutual adaptation, synchronizing to each other, with the man-machine system and further to apply it to the site of walking aid.

Another object is to provide an evaluation method for evaluating objectively the improvement effect in walking motion when the walking aid system is used.

Still another object is to provide an evaluation method for evaluating the gait objectively.

To solve the above problems, a walking aid system of the present invention includes as shown in FIG. 3 for example: a sensor section 2 for sensing the motion rhythm of a walker; a recording section 33 for recording measurement values of the motion rhythm sensed with the sensor section 2; a target setting section 34 for setting a target value for the motion rhythm of the walker; a timing generating section 36 for generating a timing signal according to both the measurement and the target value; and a stimulus generating section 4 for generating rhythm stimulus that is recognizable by the walker, according to the timing signal generated with the timing generating section 36.

Constituting as described above makes it possible to apply mutual adaptation, synchronizing to each other, to the man-machine system and further apply it to the site of walking aid.

In a preferred embodiment of a walking aid system of the present invention, as shown in FIG. 4 for example, the motion rhythm of the walker and the timing signals constitute a nonlinear synchronized state; and the target value is used as a parameter for changing the synchronized state.

Constituting as described above makes it possible to constitute a nonlinear control system (relative system) in which the human motion rhythm and the timing signal of the walking aid system synchronize to each other to control the synchronizing frequency and period toward desirable direction by giving such a synchronized state a target value. Appropriately adjusting the target value of this system permits application to assisting walkers in various states of disability.

The control of the nonlinear system is realized only by the use of the relative system. The following relational system control method is introduced to this walking aid system. That is, a main section includes a nonlinear system module (NLS module) 13 having dynamic behavior as a nonlinear system and a feedback system module 14 performing feedback to the nonlinear system module 13. The nonlinear system module 13 establishes a synchronized state through entrainment in interaction between itself and a walker 12, a controlled object having also the characteristic of a nonlinear oscillation system. The feedback system module 14, in the synchronized state between the nonlinear system module 13 and the walker 12, calculates a synchronize-related relative amount 15, calculates an appropriate feedback control amount by comparing the synchronize-related relative amount 15 with the target relative amount, and applies feedback to adjust the parameter of the nonlinear system module 13 that changes the synchronize-related relative amount 15. Thus the object 12 of control is controlled by causing the synchronize-related relative amount 15 to converge to the target relative amount in "mutually adaptive" manner.

In a preferred embodiment of a walking aid system of the present invention, the synchronized state has a entrainment phenomenon.

Here, the entrainment phenomenon is a process in which dynamics of different nonlinear oscillations adapt to each other and a phenomenon in which nonlinear oscillations of different frequencies spontaneously tend to a synchronized state through interaction. In such constitution in this way, the entrainment phenomenon in the walk motion is noticed to improve the mutually adaptive type of in-face technique, resulting in improvement of stability in the walk motion. This can find applications such as the fall prevention for the aged.

In a preferred embodiment of a walking aid system of the present invention, the target setting section 34 is made adjustable for the target value from outside; and the difference between the motion rhythm and the rhythm stimulus is made adjustable.

Here, the phrase "adjustable from outside" includes the possibility of setting input from outside and adjustability using a pushbutton, variable resistor, etc. Constituting in this way makes it possible to adjust timing discrepancy between ground contact of foot and sound stimulus. When this is applied to accelerated walk or cowering appearing with Parkinson's disease, it is possible to prompt or restrict walk motion for improving these disabilities.

In a preferred embodiment of the present invention, a walking aid system includes the sensor section 2 has sensors 21 on left and right feet respectively; the respective sensors 21 sense measurements of motion rhythms of the left and right feet respectively; the target setting section 34 is capable of setting target values for left and right rhythm stimuli, respectively; the timing generating section 36 generates timing signals related to left and right rhythm stimuli according to combinations of two sets of measurements and target values, respectively; and the stimulus generating section 4 generates rhythm stimuli at left and right ears or eyes according to the respective timing signals.

Constituting as described above makes it possible to control individually the walk motion of left and right legs, to apply it to asymmetric walk disability such as hemiplegic walk or the like, improving these walk disabilities.

In a preferred embodiment of a walking aid system of the present invention, as shown in FIG. 1 for example, the sensor section 2 has an acceleration sensor; the stimulus generating section 4 generates as rhythm stimuli: vocal stimuli, optical stimuli or functional electric stimuli; and the main section 3 is of a portable type and has the recording section 33, the target setting section 34, and the timing generating section 36.

Constituting as described above enables a constitution in which the walking aid system may be attached to walkers including the walk-disabled, assisting rehabilitation using the walking aid system.

The walking aid evaluation method of the present invention comprises the steps of: sensing the motion of a walker P with a sensor; obtaining the walk locus of the walker P from the sensed motion; and evaluating the improvement effect of the walking aid from change with time in the evaluation index related to the walk locus.

Constituting as described above makes it possible to evaluate improvement effect in walk motion when the walking aid system is used. It is also adaptable to a case in which a walking aid system using mutual adaptation is used. First, from the time series data of evaluation indices for the walk motion of individual patients, improvement effects for individual patients can be evaluated. For example, it is possible to evaluate hemiplegic walk caused by left-right asymmetry in walk motion. If step period is chosen as the evaluation index, it is possible to evaluate accelerated walk and cowering from the change in the period with time. Second, from the change in the evaluation index before and after the use of the walking aid system, effect of using the system can be evaluated. In this case, if the target value is made to vary diversely, it is possible to evaluate how the setting is to be made to increases the effect. From the above, appropriate evaluation of the improvement effect with the walking aid is expected. Because analysis process is carried out using computers, real time evaluation is also possible.

In a preferred embodiment a walking aid evaluation method of the present invention, asymmetry in the walk locus or the ratio of step-back to displacement is used as the evaluation index.

Constituting in this way, evaluation results are obtained with high accuracy and efficiency.

The gait evaluation method of the present invention comprises the steps of: sensing the motion of a walker with a sensor; obtaining the walk locus of the walker from the sensed motion; and evaluating the gait of the walker from the change with time in the evaluation index related to the walk locus.

Constituting in this way, a method of objectively evaluating the gait of the walker is provided.

According to the present invention, mutually synchronizing, cooperating relation can be realized with a man-machine system, which can be applied to the site of walking aid.

Further, it is possible to evaluate the improvement effect of the walk motion in the case the walking aid system utilizing mutual adaptation is used.

This application is based on the Patent Applications No. 2004-293136 filed on Oct. 5, 2004 in Japan, the contents of which are hereby incorporated in its entirety by reference into the present application, as part thereof.

The present invention will become more fully understood from the detailed description given hereinbelow. However, the detailed description and the specific embodiment are illustrated of desired embodiments of the present invention and are described only for the purpose of explanation. Various changes and modifications will be apparent to those ordinary skilled in the art on the basis of the detailed description.

The applicant has no intention to give to public any disclosed embodiment. Among the disclosed changes and modifications, those which may not literally fall within the scope of the patent claims constitute, therefore, a part of the present invention in the sense of doctrine of equivalents.

The use of the terms "a" and "an" and "the" and similar referents in the context of describing the invention (especially in the context of the following claims) are to be construed to cover both the singular and the plural, unless otherwise indicated herein or clearly contradicted by context. The use of any and all examples, or exemplary language (e.g., "such as"), provided herein, is intended merely to better illuminate the invention and does not pose a limitation on the scope of the invention unless otherwise claimed.

BRIEF DESCRIPTION OF THE DRAWINGS

FIG. 7($a$) shows left-right fluctuation of the center of gravity of the body during a walk. FIG. 7($b$) shows the impulse calculated from the floor reaction force in the support leg period.

FIG. 13($a$), FIG. 13($b$) and FIG. 13($c$) show respectively resultant loci of walk at speeds the walker felt to be slow, normal and fast.

FIG. 14($a$), FIG. 14($b$), FIG. 14($c$) and FIG. 14($d$) show the cases when walk parameters as indices are indices Xa, Y'$_L$, Za and Ta.

FIG. 15($a$), FIG. 15 ($b$), FIG. 15($c$) and FIG. 15 ($d$) show the walk loci of the quasi-patient Q before the use of the walking aid system, the walk loci of the quasi-patient Q in use of the walking aid system, the walk loci of the patient A before the use of the walking aid system, the walk loci of the patient A in use of the walking aid system.

Figure 1:
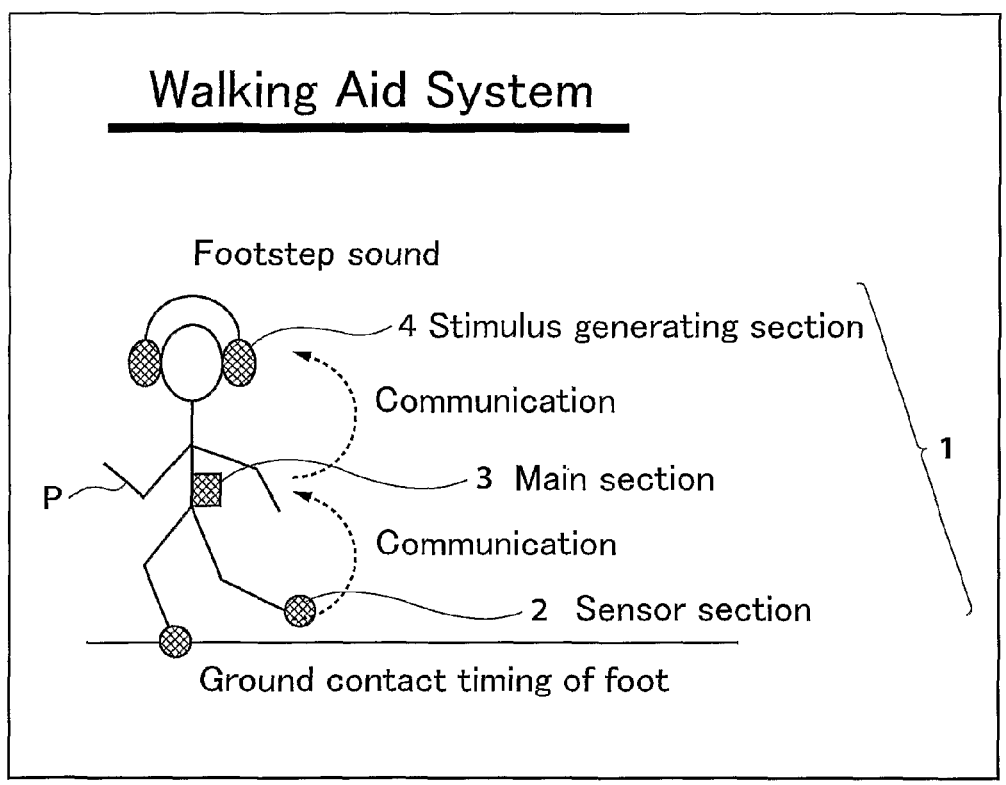
FIG. 1 is a schematic view, for describing a walking aid system.

1: walking aid system 2: sensor section 2L, 2R: left sensor, right sensor 3: main section 3A: portable computer 3B: wireless conversion unit 4: stimulus generating section 5: algorithm 9: network 10: nonlinear system 11: controller 12: controlled object 13: nonlinear system module 14: feedback system module 15: relative amount 16: motion rhythm 17: rhythm stimulus 21: sensing section 24: signal output section 31: input section 32: interface section 33: recording section 34: target setting section 35: operating section 36: timing generating section 37: output section 38: control section P: walker

BEST MODE FOR CARRYING OUT THE INVENTION

Embodiments of the invention are hereinafter described in reference to the accompanying drawings.

FIG. 1 is a schematic view for describing a walking aid system 1 as a first embodiment of the invention. The first embodiment is an example of utilizing the system in the walking aid for the aged and the physically handicapped. A walker P carries a sensor section 2 with an acceleration sensor on left and right ankles, a main section 3 on the waist, a stimulus generating section 4 such as headphone on the head. The entire walking aid system 1 is made as a wearable unit. Its main section 3 mainly consists of a portable computer storing a control program (algorithm 5) for the walker. The main section 3 receives measurements of walk rhythm as motion rhythm from the sensor section 2, generates timing signals based on the measured walk rhythm and the target value of the walk rhythm preset for the walker, and send to the headphone 4 rhythm sound as rhythm stimulus using the timing signals. Communication between the main section 3 and the acceleration sensor 2, and between the main section 3 and the headphone 4 is performed through wired or wireless communication, for example blue-tooth or the like. The walker P walks while listening to the rhythm stimulus through the headphone 4.

The portable computer of the main section 3, using the algorithm 5, creates a virtual robot of a virtual space. The virtual robot generates rhythm sound from the timing signal. The walk rhythm is synthesized into footstep sound, so that the walker P feels like walking with someone else side by side. In other words, a co-creative type of interface technique is used in the process of physical interaction through the exchange of footstep sound between the virtual robot and the walker P in a real space. This is to realize stabilization of walk motion of the walker P by synchronizing together the walk rhythm of the robot and the walker P. In this way, it is possible for the aged to prevent from falling and also possible to alleviate various symptoms of walk-disabled people due to Parkinson's disease and hemiplegia, for example.

Figure 2:
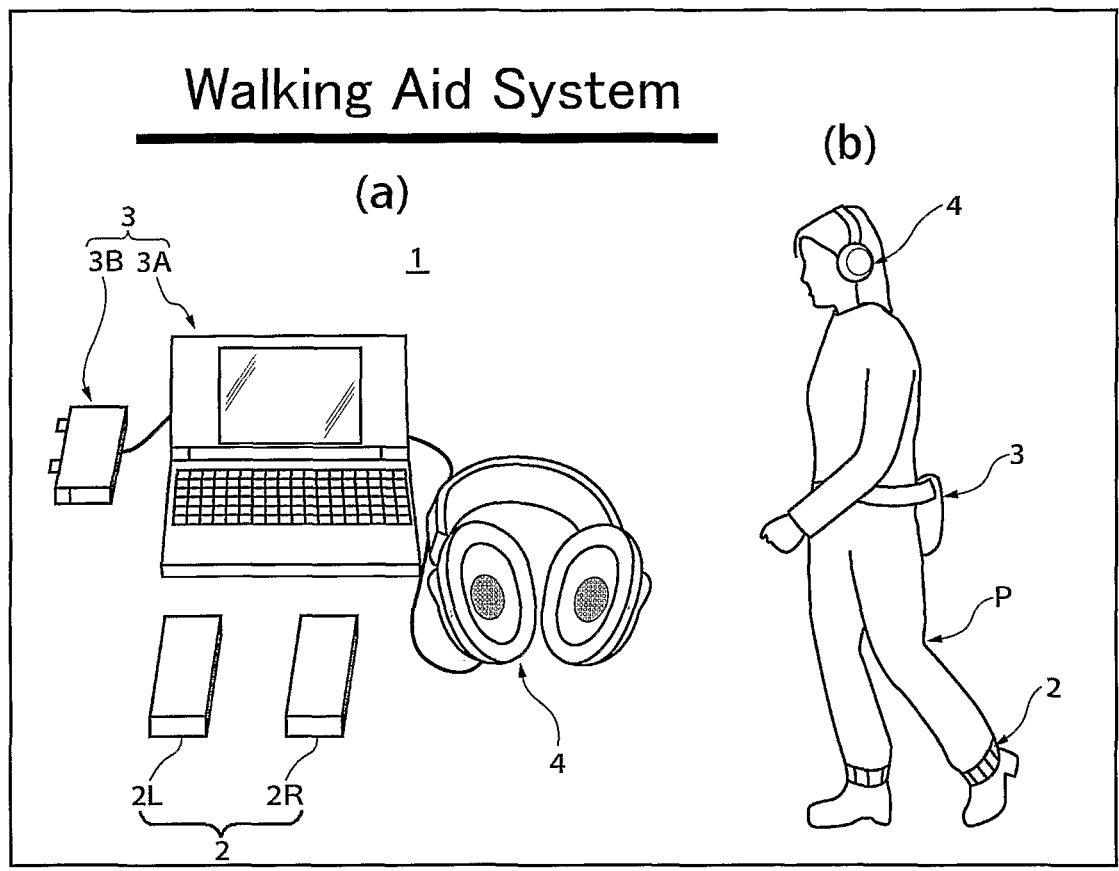
FIG. 2 exemplifies an external view of the walking aid system.

FIG. 2 exemplifies an external view of the walking aid system 1. FIG. 2(a) shows external view of various devices constituting the walking aid system 1. FIG. 2(b) shows the walker P carrying the walking aid system 1. The sensor section 2 is attached to each of left and right ankles and has an acceleration sensor, a CPU, a wireless module, a battery, etc. mounted thereon. The main section 3 is comprised of a portable computer 3A and a wireless conversion unit 3B. A wireless module for communicating with the left and right sensor sections 2L and 2R, a CPU, and a USE controller for communication with the portable computer 3A is mounted on the wireless conversion unit 3B. The portable computer 3A has a CPU and a memory for calculating timing according to information from the sensor sections 2 and for feeding back rhythm sound to the walker. A headphone 4 serves as a stimulus generating section for feeding back rhythm sound to the walker.

As for making the walking aid system 1 wearable, the sensor section 2 in conventional models has had a problem in wearability due to its size and weight, therefore requiring reduction in size and weight. The acceleration sensor is adopted on conditions that: among various types of sensors capable of measuring walk motion, downsizing is easy and no unnatural burden is imposed to the walker associated with measurement. A three-axis acceleration sensor is attached to the ankle to form a small system for measuring leg motion. The sensor section 2 weighs about 60 grams to permit use for continuous 6 hours or longer.

The walking aid system 1 comprises the sensor section 2 and the main section 3. In the conventional model, these two subsystems are interconnected through a cable. Therefore, problems in safety is pointed out that the conventional model in that state is not only hard to use but involves danger of the cable tangling with the walker's legs. To solve this, cordless design has been realized using a weak radio wave system. In the current state, it is possible to transmit signals wirelessly over a distance of 20 to 30 meters, extend up to 40 channels, without interference with medical appliances. As a result, it has been made possible to completely separate the sensor section 2 from the main section 3. Further, attachment of the walking aid system 1 to the walker P has become very easy and there is no restriction on physical motion.

Figure 3:
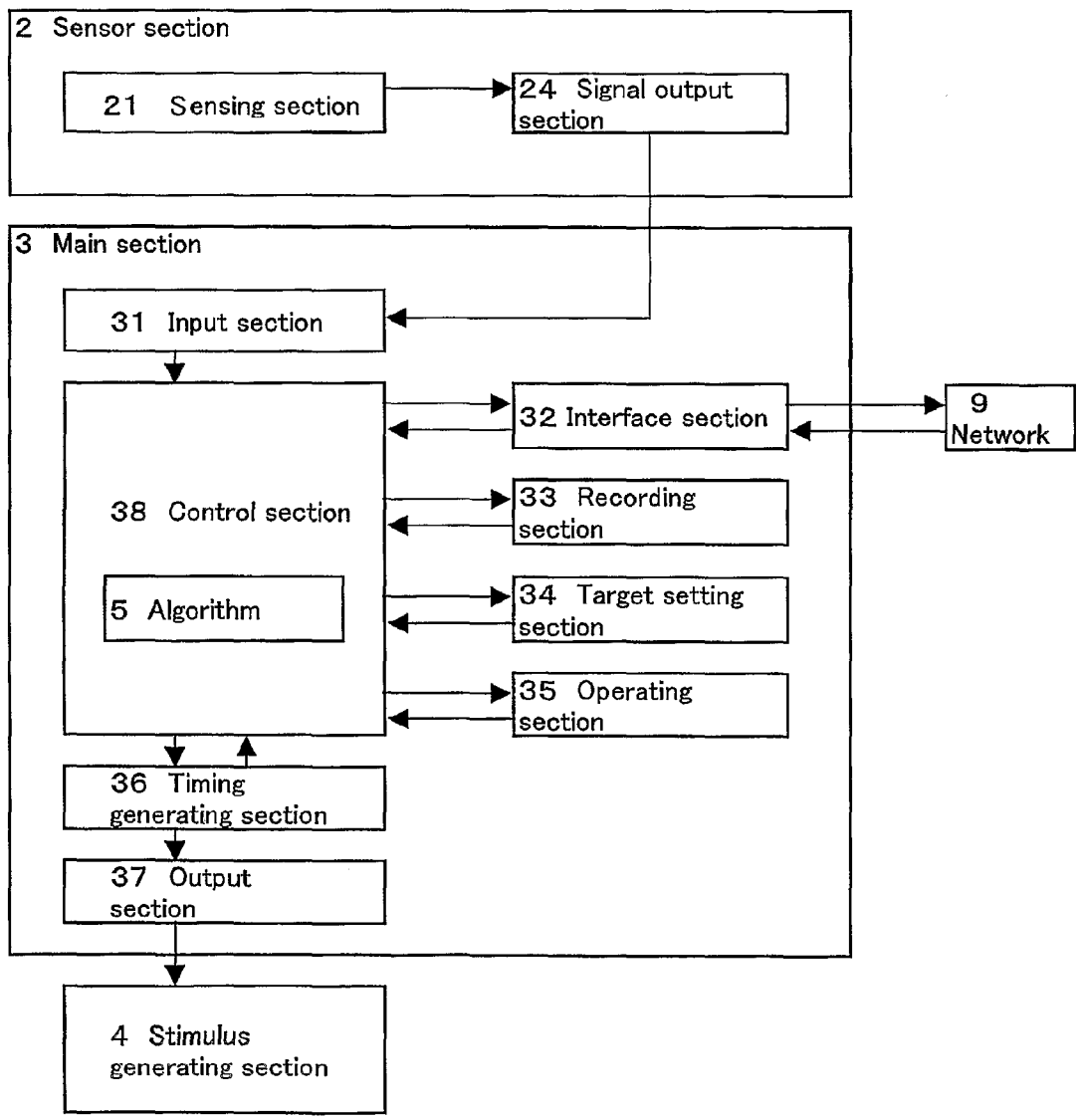
FIG. 3 exemplifies a constitution of the walking aid system.

FIG. 3 exemplifies a constitution of the walking aid system 1 of the first embodiment.

The sensor section 2 has one or more sensors for sensing various kinds of information on the motion and physical conditions of the walker, and comprises a sensing section 21 and a signal output section 24.

The sensing section 21 uses a motion rhythm sensing sensor to sense motion rhythm such as leg motion and waist sway accompanying the walk motion. For example, it is possible to obtain information on the walk rhythm (such as period) and ground contact timing of foot by sensing acceleration change time with acceleration sensor attached to the ankle or waist of the walker. Further for example, the ground contact timing may be sensed using a pressure sensor, or walk rhythm may be sensed with a pedometer or the like.

A sensor (not shown) for sensing physiological information (physical condition) of the walker may be added to the sensing section 21 to sense the physiological information such as pulse, respiration, and myoelectric potential of the walker, together with the motion rhythm sensing. This makes it possible to control the physical condition of the walker and provide walking aid and walk rehabilitation without coercion.

The signal output section 24 applies, if necessary, appropriate pre-process such as noise removal to the information sensed with the sensing section 21 and sends the information as measurements to the main section 3. To send the signals, wired or wireless connection is used depending on the locations of attaching the sensors. In particular when the sensor section is attached to the leg or waist, ease of attaching the sensor and safety are improved by employing wireless connection. Wireless connection further makes it possible to attach a plural number of sensors to various locations on the same walker. This is convenient for sensing various information.

The main section 3 performs operation process according to various information sensed with the sensor section 2, and produces timing signals. In other words, based on the motion information and physiological information sensed with the sensing section 2, timing control is performed to realize the target value of motion rhythm, the stimulus generating section 4 is made to generate rhythm stimulus such as rhythmical sound or music so as to control the walk of the walker. The main section 3 has an input section 31, an interface section 32, a recording section 33, a target setting section 34, an operating section 35, a timing generating section 36, an output section 37, and a control section 38.

The input section 31 receives the motion information and physiological information sensed with the sensing section 2 as measurements. The information received is stored in the recording section 33 to be used for operation in the operating section 35 and the timing generating section 36. To receive this information, wired or wireless means is used depending on the attachment locations of respective sensors.

The interface section 32 functions as both human interface and network interface. As a human interface, it performs setting and adjustment of target values of motion rhythms such as walk rhythm (such as period) and ground contact timing when buttons and knobs provided on the main section case are operated. Further, the section may be connected to a stationary personal computer (not shown) before walking to set target values from the stationary personal computer and then separate it from the personal computer to use it while walking. The target values set are recorded in the target setting section 34. Using the stationary personal computer makes it possible to use target values operated with the personal computer according to the previous data of the walker, to set target values by referring to data on the aged, the walk-disabled, the normal people and many other walkers, and to use them for the walk data analysis.

When it is connected through wireless to the stationary personal computer, it can be used during a walk to perform a large amount of operation process with the personal computer and send the data to the main section 3. When the wireless is used, it is also possible to connect to external personal computers via a network.

The recording section 33 records motion information data such as walk rhythms and physiological information data coming sent from the sensor section 2. It also stores motion information and physiological (physical condition) information on the walk rhythm (such as period), ground contact timing, walk distance, and walk speed, as measurements, calculated from those data in the operating section 35. Further, the information related to the target values may be stored in duplicate in the target setting section and in the recording section. For example, in the case the number of target values is great or the target values are the function of time, it is convenient to store all the data in the recording section 33, and extract part of the data required for the current walk, and store them in the target setting section. These pieces of information are used during walk in various operations in the operating section 35, and for generating timing of rhythm stimulus in the timing generating section 36. After the walk, the data stored before and during the walk using a memory card and the like may be taken out, analyzed with the stationary personal computer, and displayed. A volatile memory (RAM) or the like may be used as the recording section 33.

The target setting section 34 records target values such as motion rhythms entered by the walker and/or aiding person through the interface section 32. While motion information and physiological (physical condition) information such as the walk rhythm (such as period), ground contact timing, walk distance, walk speed, etc. may be set as target values, the number of target value (s) may be either singular or plural. Further, the walker during a walk may operate button and knobs provided on the main section to update the target values. According to the target values set, timing is calculated for generating rhythm stimulus such as rhythm sound with the timing generating section 36.

The operating section 35 calculates the walk rhythm (such as period), ground contact timing, walk distance, walk speed, etc. based on the measurements of the motion information data and physiological information data sensed with the sensor section 2. Based on the motion information data and physiological information data calculated with the operating section 35, and on the target values set with the target setting section 34, timing for generating rhythm stimulus such as rhythm sound is calculated in the timing generating section 36.

The timing generating section 36 calculates timing for rhythm stimulus such as rhythm sound according to the measurements of the motion information data and the physiological information data sensed with the sensor section 2 and to the preset target values, and generates timing signals. For example, it calculates timing for the rhythm stimulus such as rhythm sound according to the difference between the walk rhythm of the walker and the target walk rhythm, the difference between the walk speed of the walker and the target walk speed, the difference between the walk distance and the target walk distance, the difference between the measurement of the ground contact timing and the target ground contact timing, and their combination, and generates timing signals using the calculated timing. The timing signals are generated for example by frequency division of clocks from a crystal resonator. The timing signals generated are sent through the output section 37 to the stimulus generating section 4 to generate rhythm stimulus such as rhythm sound.

The timing signal is comprised of information on the rhythm tempo and information on the phase difference as the deviation from the tempo. For example, in the case walk tempo is too slow, timing signal is generated to increase the rhythm stimulus tempo or to advance the rhythm stimulus phase, and in the case walk tempo is too fast, adjustment is made to decrease the rhythm stimulus tempo or delay the rhythm stimulus phase. It is also possible to perform operations related to tempo and phase independent of each other or in any combination.

The control section 38 controls signals and data flow within the sensor section 2, the main section 3, and the stimulus generating section 4, and among them, and controls the timing for causing the stimulus generating section 4 to generate rhythm stimulus according to measurements of motion information data and physiological information data sensed with the sensor section 2 and according to the target values set with the target setting section 34, and outputs generated timing signal to the stimulus generating section 4.

The output section 37 outputs the timing signal generated with the timing generating section 36 to the stimulus generating section 4. For sending the output information, wired or wireless means is used depending on the attachment locations of the stimulus generating section 4.

The stimulus generating section 4 generates rhythm stimulus such as rhythm sound according to the timing signal received from the main section 3 and transmits it to the walker through an earphone, headphone, or speaker. To the walker, rhythm stimulus by music, other than the rhythm sound, may be used or presented, rhythm stimulus to the arm or leg through tactual sense using functional electric stimulus may be used or presented, and rhythm stimulus to the visual sense using LED (light emitting diode) or the like may be presented. It is also possible for example to display to the walker such data as walk rhythm, walk distance, and walk speed using a small size display attached to the wrist by means of a strap, or to output voice through a headphone. In this way, the walker can see the data during the walk in real time, and the data can be immediately fed back to the walk in rehabilitation.

Figure 4:
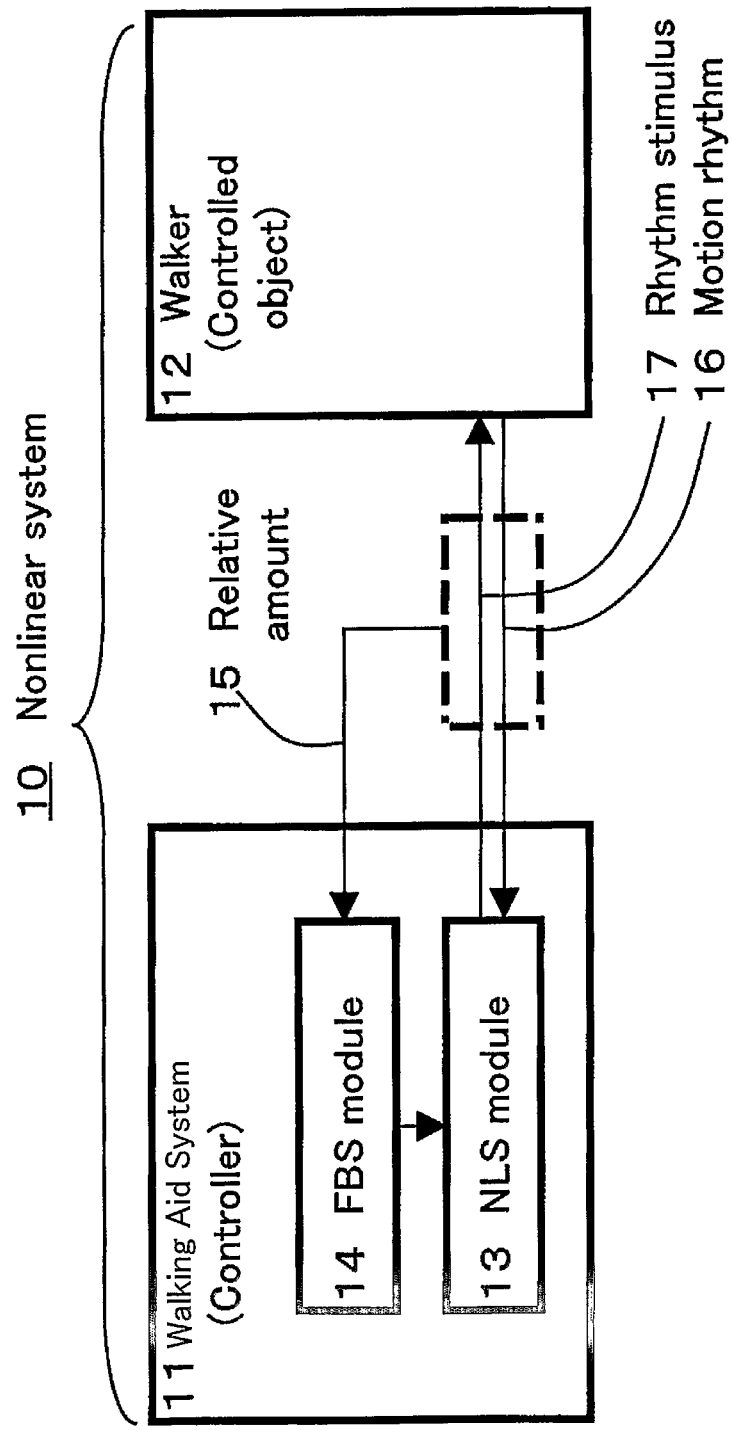
FIG. 4 is a schematic view of a nonlinear system for controlling a man-machine system.

FIG. 4 is a schematic view of a nonlinear system 10 for controlling a man-machine system.

The nonlinear system 10 is made up of a controller 11 and a controlled object 12. The nonlinearity means that the dynamics of the controller 11 and the controlled object 12 are inseparable. Conventional feedback control, as for its applicable region, is limited to linear systems, which corresponds to the fact that the controller 11 and the controlled object 12 are separable. To be separable is the very reason that the controller 11 can control the controlled object 12. In the nonlinear system 10, since both dynamics are inseparable, controlling ends up in being controlled, so that no feedback control can be established. In that sense, the nonlinear system 10 is the one hard to be controlled. However, the control is partially possible by taking note of the synchronizing relationship produced by nonlinear oscillation and its entrainment phenomenon.

The walking aid system 11 as a controller is made up of a nonlinear system module (NLS module) 13 having dynamic behavior as a nonlinear system and a feedback system module 14 performing feedback to the nonlinear system module 13. The nonlinear system module 13 establishes a synchronized state between itself and the walker 12 as a controlled object, having likewise the nature as a nonlinear oscillation system through the entrainment phenomenon in mutual action. The feedback system module 14, in the state of the nonlinear system module 13 and the walker 12 synchronizing each other, calculates a relative amount 15 for synchronizing and compares the relative amount 15 for synchronizing with a relative amount set as a target, to thereby calculate an appropriate feedback control amount, and applies feedback so as to adjust the parameter of the nonlinear system module 13 that changes the relative amount 15 for the synchronizing. In this way, the relative amount 15 for synchronizing is made to converge to the target relative amount in mutually adaptive manner, so as to control the controlled object 12. In other words, this is an application of "relational system control method" as a nonlinear system control method.

This embodiment assumes that the controller 11 and the controlled object 12 have nonlinear dynamics and produce entrainment phenomenon through mutual action to synchronize. This entrainment is a synchronizing phenomenon characteristic of the mutual interaction of nonlinear oscillation. In the process of mutual adaptation of dynamics between nonlinear oscillations of different frequencies, they lead spontaneously to a synchronized oscillation at the same frequency and constant phase relationship. Here, since the nonlinear oscillation approaches the synchronized state, it is assumed that the synchronized state contains a state that is close to the same frequency and a constant phase relationship, for example a state of the same frequency on the average and a constant phase relationship on the average.

According to this embodiment as described above, even in the case the dynamics of the controller and the controlled object cannot be clearly divided, it is possible to provide a "relational system control method" capable of causing their relative amounts to converge to a target relative amount by unifying the characteristic of the nonlinear system and the characteristic of the feed back control. In other words, it is also possible to control the nonlinear system by the use of the relational system control method.

According this embodiment (the walking aid system 1 shown in FIG. 3), the motion rhythm 16 is transmitted from the walker 12 to the nonlinear system module 13 through the sensor section 2, and the rhythm stimulus 17 is transmitted from the nonlinear system module 13 to the walker 12 through the stimulus generating section 4. The input section 31, the operating section 35, the timing generating section 36, the output section 37, and the control section 38, which are included in the main section 3, have the function of the nonlinear system module 13. The target value of the motion rhythm set with the target setting section 34 is compared with the motion rhythm measured with the sensor section 2, and the timing signal to be the base of the rhythm stimulus is generated. Therefore, the target setting section 34 has the function of the feedback system module 14. For example, it is possible to adjust pitch and timing of motion by assuming the phase difference of the motion rhythm to be the relative amount and the target value of the motion rhythm to be a parameter.

The walking aid system of this embodiment is a co-creating type of walking aid system by means of which a virtual robot in a virtual space in a computer and a walker in a real space walk in synchronize with each other through footstep sound and as a result the walk motion is stabilized. Although there occurs nothing more than that the footstep sound of the walker is transmitted to the virtual robot and the footstep sound of the virtual robot is returned to the walker, the walker's walk rhythm synchronizes with the virtual robot's walk rhythm. While it is daily experienced that, when one walks someone else side by side, both persons naturally come to walk in step with each other, this embodiment is to improve likewise the walker's walk through the synchronizing phenomenon between the human walk rhythm and the virtual robot's walk rhythm.

Figure 5:
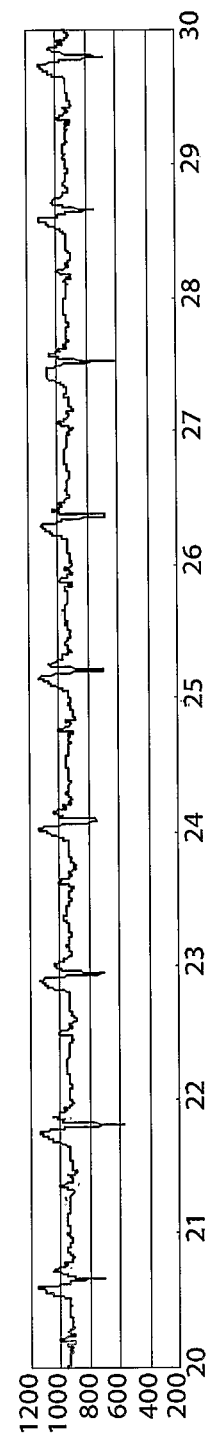
FIG. 5 shows an example of a state of walk monitored with an acceleration sensor.

FIG. 5 shows an example of state of a walk monitored with an acceleration sensor of this embodiment. The vertical axis represents acceleration and the horizontal axis represents time. FIG. 5 shows the change in acceleration of the leg motion with time. The point where particularly abrupt change is seen corresponds to the timing of ground contact, evidencing that the state of walk is monitored by sensing the ground contact timing of the foot with this acceleration sensor.

Next, application to fall prevention was examined.

Fall prevention during walk was examined from the need of improving stability in the walk motion. The walk motion is a rhythmic motion. Stability was attained by realizing mutual action between the patient and the aiding device through rhythm. Specifically, four ways of aid methods (algorithms) were compared.

Table 1 shows the results of comparison.

(A) is the case of simple feedback in which the patient listens to the leg motion rhythm directly as auditory sense stimulus. (B) is the case of walking in step with constant tempo rhythm sound like a metronome. (C) is the case of walking with the internal rhythm of the aid system and the patient's walk rhythm synchronizing each other by entrainment. (D) is the case in which deviation in synchronize timing is controlled in addition to the effect of (C) to control prompt and restriction of the walk motion. The data of S1 and S2 are averages of variation width of fluctuation of the walk period of the patient. The data S1 were taken before the use of the walking aid system and the data S2 during the use. The letter "p" denotes an index which shows the degree of decrease in fluctuation based on data difference between S1 and S2; the smaller the index "p," the greater the effect. From these results of comparison, (A) and (B) do not show much effect, (C) shows some effect with the index p not greater than 0.05, and in particular (D) shows great effect with the index "p" not greater than 0.01, proving the effectiveness of the algorithm.

Figure 6:
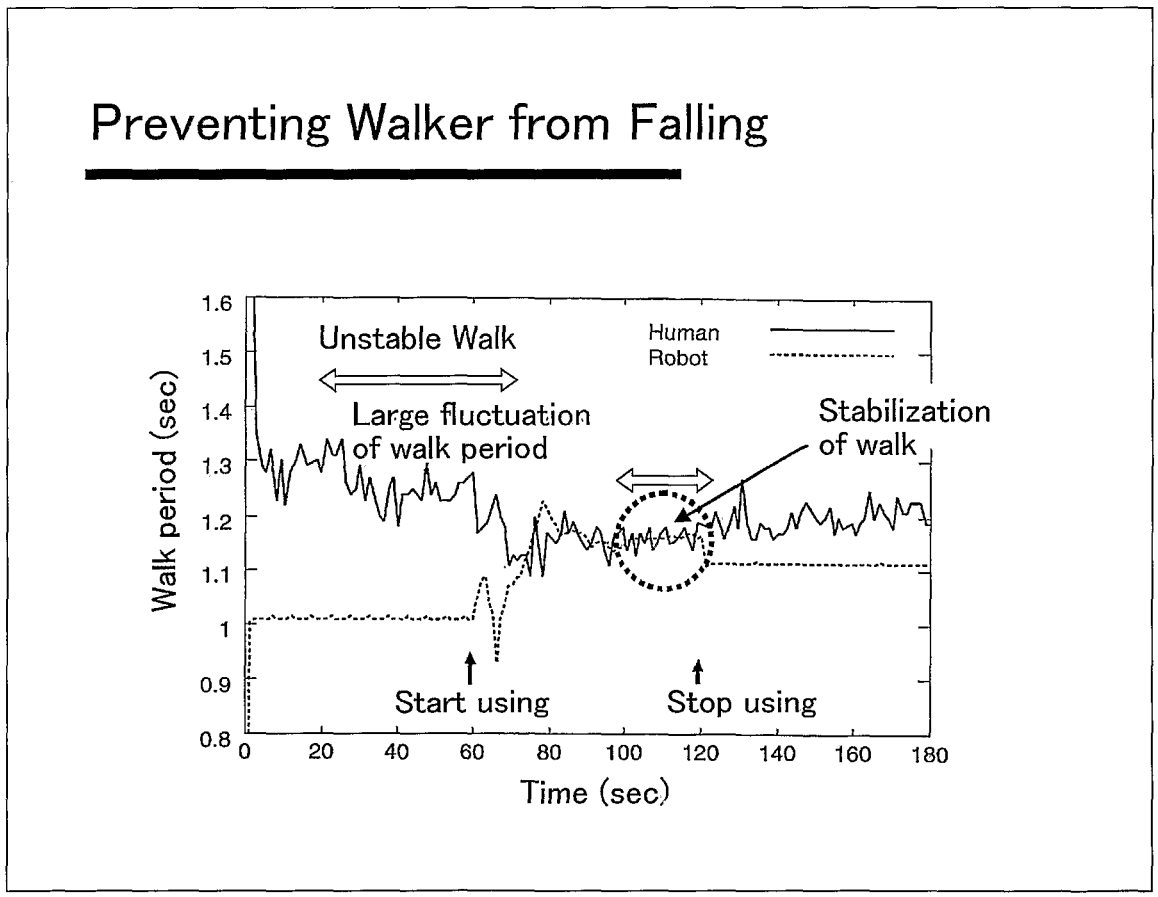
FIG. 6 shows an example of fall prevention effect of the walking aid system during a walk.

FIG. 6 shows an example of fall prevention effect of the walking aid system during a walk. The vertical axis shows walk period (in seconds) and the horizontal axis shows time (in seconds). While the walk period fluctuates greatly before the use of the aid system, it becomes almost constant after starting the use (indicated with arrow), meaning that the walk is stabilized. The stabilized state lasts also after stopping the use (indicated with arrow). Thus, the system is capable of stabilizing unstable walk motion and applicable to the fall prevention for the aged.

Next, application to hemiplegia was examined.

The hemiplegia is motion paralysis of one side of the body, left or right, due to disorder in cerebral blood vessels or muscular skeletal system. For this case, it is expected that the application of mutual adaptation process of the walking aid system individually to left and right legs improves the balance between left and right legs, so as to alleviate walk disability of left-right asymmetry such as the hemiplegia.

From the viewpoint of the walking aid, since instability in the walk motion results from asymmetry of motion of left and right legs, importance of counterbalancing has been pointed out. Therefore, algorithm was used for the cases (A)-(D) for comparison, like the cases of the fall prevention evaluation.

Table 2 shows the results of comparison. The data of S1 and S2 are those for the asymmetry in ground contact timing of left and right legs of the patient (difference between the period of time from the ground contact of the right foot to the ground contact of the left leg and the period of time from the ground contact of the left foot to the ground contact of the right leg). It shows that the greater the absolute value, the greater the degree of asymmetry, and smaller the absolute value, the greater the degree of symmetry. One of the signs + and − represents a longer time from the right foot ground contact to the left foot ground contact, and the other represents contrary. The letter p denotes an index which shows the degree of decrease in asymmetry based on data difference between S1 and S2; the smaller the index p, the greater the effect. The data S1 are those before the use of the walking aid system, and the data S2 during the use. From these results of comparison, (A), (B), and (C) do not show much effect, while (D) shows great effect, with the p being not greater than 0.01. Like the case of Table 1, the algorithm (D) proved its effectiveness. In particular the effectiveness of the algorithm was shown in improving the balance between both legs by prompting the motion of the affected leg (disabled side of leg) and restricting the motion of the healthy leg (leg on the side free from disability).

Further, motion dynamics analysis was made to the algorithm (D) to examine its effectiveness also from a dynamic level.

Figure 7:
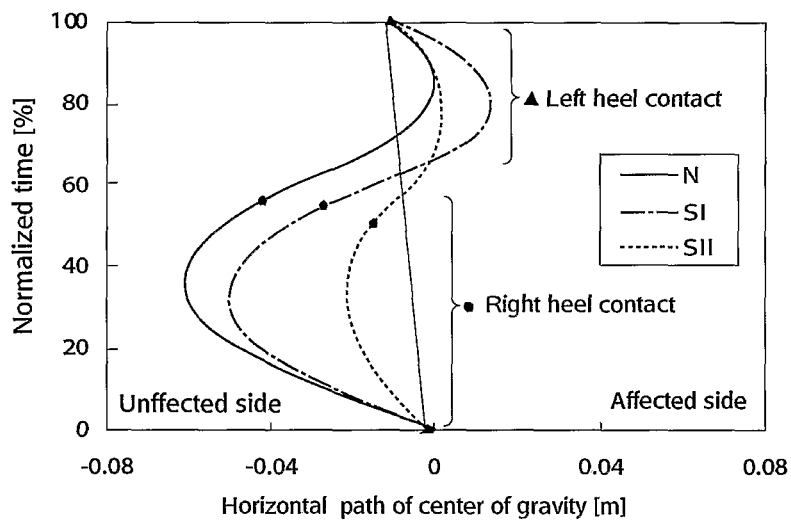
FIG. 7 shows an example of results of motion dynamics analysis related to the application to the hemiplegia.
Figure 7:
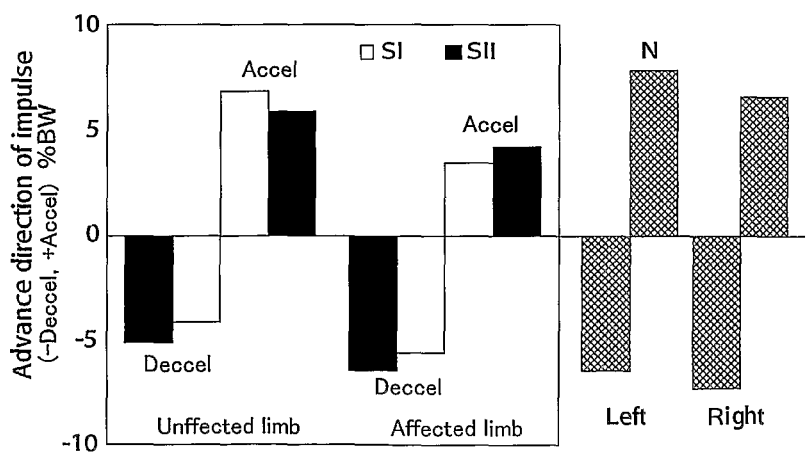

FIG. 7 shows an example of results of motion dynamics analysis related to the application of the algorithm to the hemiplegia. FIG. 7(a) shows left-right fluctuation of the center of gravity of the body during a walk. The vertical axis represents normalized time, and the horizontal axis represents fluctuation. The curve N shows the locus of center of gravity of a normal person; the curve S1, the locus of center of gravity of a patient before the use of the walking aid system; and S2, the locus of center of gravity of the patient during the use of the walking aid system. As can be seen, the left-right fluctuation of center of gravity decreases with the use of the walking aid system, showing effectiveness for stabilization.

FIG. 7(b) shows the impulse calculated from the floor reaction force in the support leg period. The vertical axis represents the impulse; the upper side corresponds to the acceleration side (when the leg leaves the ground), and the lower side corresponds to the deceleration side (when contacting the ground). The curve N shows the impulse for a normal person; S1, the impulse for the patient before using the walking aid system, and S2, the impulse for the patient when using the walking aid system. In comparison with S1, S2 is seen with an increase in the impulse on the disabled side, and a decrease on the healthy side. Thus, improvement in dynamic left-right balance was verified for the support leg period.

Next, application to Parkinson's disease was examined.

The Parkinson's disease is caused by disorder in the basal ganglia of the brain and accompanied by disturbance in generating walk motion rhythm. In particular, the "cowering" at the beginning of walk, and the "accelerated walk" not allow a person to stop once he or she starts walking, are important from the viewpoint of the walking aid.

This is a disturbance caused by Parkinson's disease or the like in the motion control process through the nerve system. It is necessary that the walking aid system is capable of controlling the phase relationship of the walk rhythms of both the walker and the walking aid system by the mutual adaptation process. It is considered that the walk motion is prompted when sound stimulus is given prior in phase to the foot ground contact and in contrast the walk motion is restricted when sound stimulus is given in the opposite phase. This makes it possible to prompt the walk motion in the state of cowering, and restrict in the state of accelerated walk. Here, evaluation was made concerning the walking aid to the accelerated walk.

Figure 8:
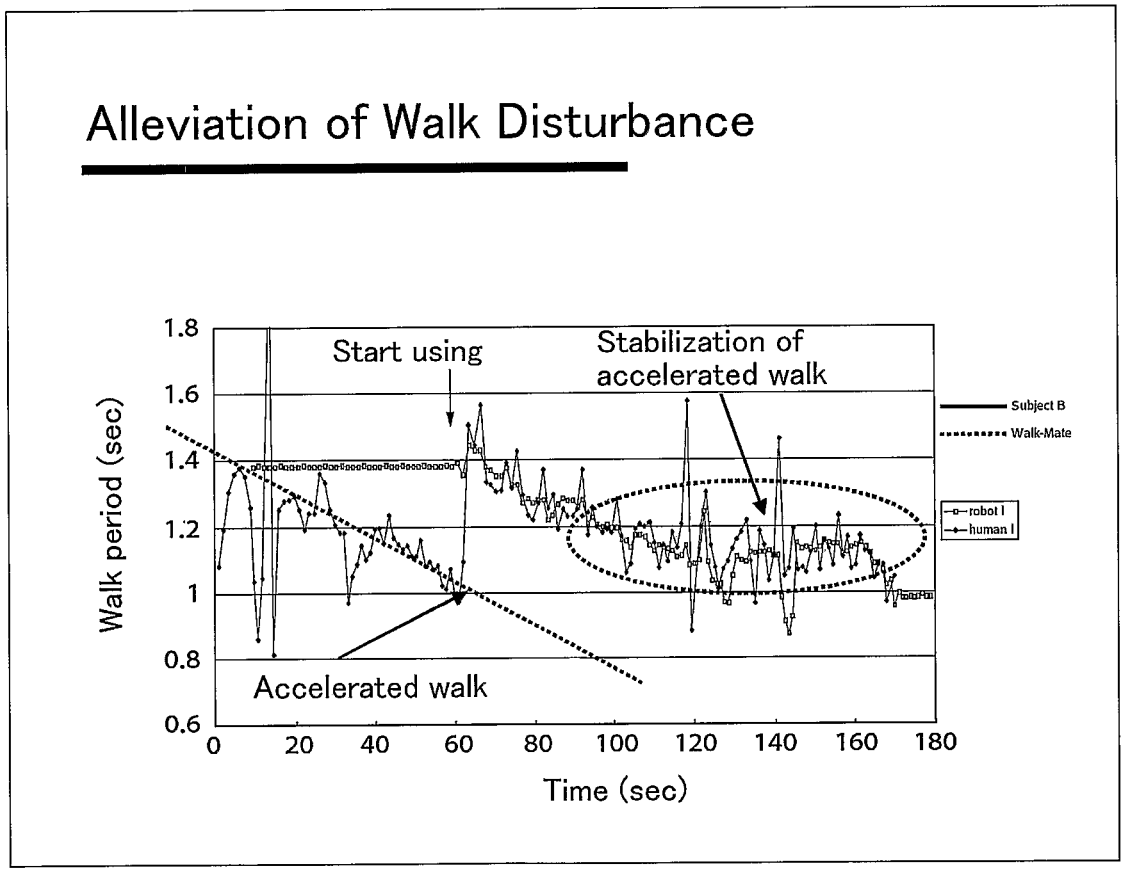
FIG. 8 shows an example of effect of alleviating the accelerated walk.

FIG. 8 shows an example of alleviating effect of the accelerated walk by means of the walking aid system. The vertical axis represents walk period and the horizontal axis, time. The algorithm used was that of (D) that controls the timing deviation at the time of synchronizing so that the rhythm on the walking aid device side synchronizes with that on the patient side with a little delay. Before the use, accelerated walk was observed in which fluctuation of the walk period was great and the walk period decreased gradually. It was also observed that the period stabilized to an approximately constant value over a period of time of about one minute from the start of walk of synchronizing with the walking aid system (indicated with arrow in FIG. 8) and also that fluctuation decreased. Incidentally, in separate measurements, it was verified that the stabilized state remained for some period of time after stopping the use of the walking aid system. This shows that the use of this walking aid system is effective in preventing the accelerated walk resulting from the Parkinson's disease.

Next is described a second embodiment. The second embodiment is an example of evaluating the walking aid. The walking aid system of this embodiment is almost the same as the first embodiment in constitution, except that the acceleration sensor is attached to the waist, and algorithm for evaluation is added to the control section. While the acceleration sensor was attached to the abdomen in some occasions, unless otherwise noted, it was attached to the waist.

In this embodiment, the walking aid system of the first embodiment is used to sense the motion of the walker P, with the acceleration sensor used in the sensor section 2. The walk locus of the walker P is obtained from the sensed motion, and the effect of the walking aid is evaluated from the change with time in the evaluation index related to the walk locus.

The walking aid system of this embodiment is to be called as Walk-Mate. This is a harmonized walk system capable of prompting or restricting the walk pace by the use of mutual adaptation process in which human walk rhythm and virtual robot walk rhythm are entrained each other.

Heretofore, the Walk-Mate has been applied to the walk-disabled to evaluate effectiveness through analysis on the aspects of time and dynamics. However, for the intention of clinical application of the system as a walking aid appliance, correspondence to analysis and evaluation carried out clinically is indispensable.

Clinical walk analyses are made mainly through visual observation on the patient's walk by doctors and physical therapists to understand disability and to judge remedial effects. However, visual analyses involve drawbacks of individual personal differences due to experience, lacking objectivity. On the other hand, motion dynamics analyzing devices on a very large scale such as optical position measurement device and floor reaction force device have been used for research purposes. To solve this problem, it is necessary to measure quantitatively the patient's walk and evaluate it. The dynamics analysis is one of the quantitative evaluation methods using optical measurements. However, since the apparatuses are inherently expensive and of a large scale, locations and measurement time are limited. Because of great mental and physical burden on the patient, it has been difficult to evaluate changes within a long period of walk and restoration amount transition of walk over a long period of time. In effect, there has been lack of evaluation method in the intermediate region between subjective evaluation on the aid site and study purpose evaluation. Therefore, it is required to develop a new evaluation method based on time series data on bioengineering information measured by the method of the present invention.

The method of this embodiment uses an acceleration sensor. The resultant acceleration waveform is used to obtain the walk locus of the attachment position. The dynamics analysis is made from the locus. Since the acceleration sensor is small-sized and lightweight, it puts little load on the patient when it is carried by the patient during walk training, and there is no need of restricting its position, so that it is possible to measure easily development with time over extended period of time. In the method for obtaining positions and displacements from an acceleration sensor, accumulation of error due to ground contact and the acceleration of gravity has been a problem. Prior studies are widely carried out to eliminate such error. In recent years, owing to the improvement in performances such as accuracy and resolution of the acceleration sensor, it has been made possible to obtain more accurate acceleration information.

On the basis of the above background here, the walk locus is calculated from the acceleration information to create an index using motion dynamics aspect compared with clinical walk analysis, to understand disability, and to evaluate transition of restoration amount due to the walk training. It has been decided to go ahead with effectiveness evaluation by adding evaluation from the motion dynamics aspect from the change in gait owing to the use of the walking aid system, Walk-Mate to both the time aspect and dynamics aspect carried out heretofore.

Next, the walk locus calculation method is described.

Figure 9:
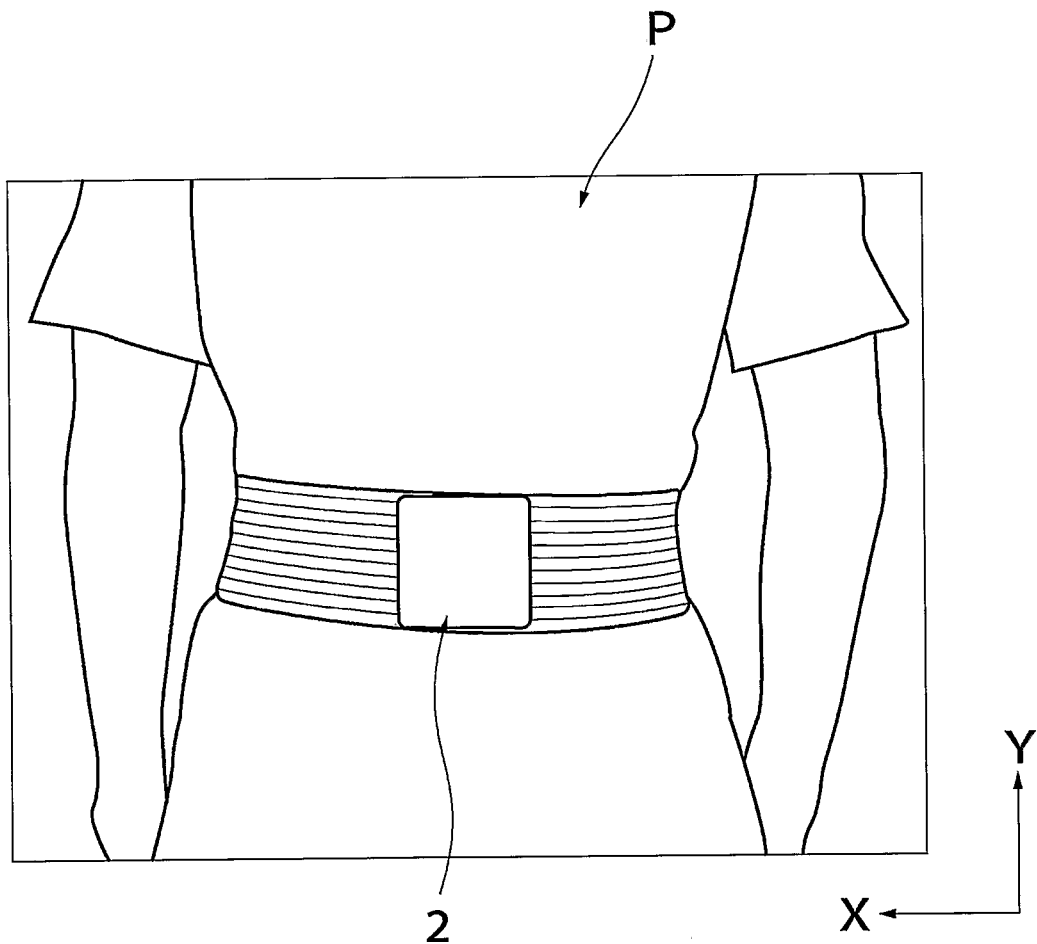
FIG. 9 shows an example of attachment state of the acceleration sensor of a second embodiment.

FIG. 9 shows an example of attachment state of the acceleration sensor of this embodiment. For the measurement method proposed here, a three-dimensional acceleration sensor 2 is used. The acceleration sensor is attached to the waist of the walker P to measure acceleration information and obtain the walk locus. Attaching it to the waist can reduce noise generated in the acceleration sensor 2.

A space coordinate system of the sensor attached to the waist is assumed with left-right direction to be X (left side being positive), vertical direction, Y, and advancing direction, Z. Acceleration in each of the three-dimensional directions is integrated to obtain speed and positional information. However, when simple integration such as the equation (1) is used to obtain speed V from acceleration A, offset error due to ground contact accumulates undesirably. Therefore, a method is proposed that the walk motion in vertical, left, and right directions is assumed to be periodic oscillating motion by the alternation of both legs, and from the walk period, a baseline to be a locus center is calculated, and the locus is obtained by integrating the amount of deviation from the calculated value.

For Vertical Direction: As factors that cause error when integrating the acceleration information, the influence of the acceleration of gravity and the impact at the time of ground contact can be pointed out. They affect particularly the error in the vertical direction. However, because the walk motion here is restricted to that on a horizontal plane, when one pays attention to the vertical direction, the height of the waist in the leg ground contact in the walk motion should be always constant. Therefore, with the equation (2) an average value of the speed Vy for a short time duration of about one second before and after a certain time point of walk is obtained, and the average value is assumed to be the baseline, the zero-point, of the walk motion, and deviation from the average value, speed V'y, is integrated to obtain the speed Vy, with error eliminated. Similar calculation is made for the integration of position to obtain Y'.

$$V_y(t) = \int A_y(t) dt \qquad (1)$$

$$V'_y(t) = V_y(t) - \overline{V_y(t)} = V_y(t) - \frac{1}{2}\int_{t-1}^{t+1} A_y(t) dt \qquad (2)$$

For Lateral Direction: As for the left-right direction, in contrast to the vertical direction in which the waist height is always constant at the time of ground contact of the leg, the walk locus tends to deviate from the preset course. Therefore, the walk analysis in the left-right direction needs to be made separately for a short term walk locus change in every step and for the tendency of deviating left and right from the course from a long term standpoint. The calculation of the displacement X is made with the equation (3) with which the speed is integrated, and the speed is calculated in the same manner as with the equation (2). The walk locus aligned to the center in every step is calculated from the equation (4) using the average $X_{1sec}$ for the short period of time (period of one second each before and after the moment). The tendency of deviating from the course is calculated from the equation (5) using the average $X_{5sec}$ for a long period of time (period of five seconds each before and after the moment).

$$X(t) = \int V_x(t) dt \qquad (3)$$

$$X'(t) = X(t) - \overline{X_{1sec}(t)} = X(t) - \frac{1}{2}\int_{t-1}^{t+1} V_x(t) dt \qquad (4)$$

$$X''(t) = X(t) - \overline{X_{5sec}(t)} = X(t) - \frac{1}{10}\int_{t-1}^{t+1} V_x(t) dt \qquad (5)$$

Figure 10:
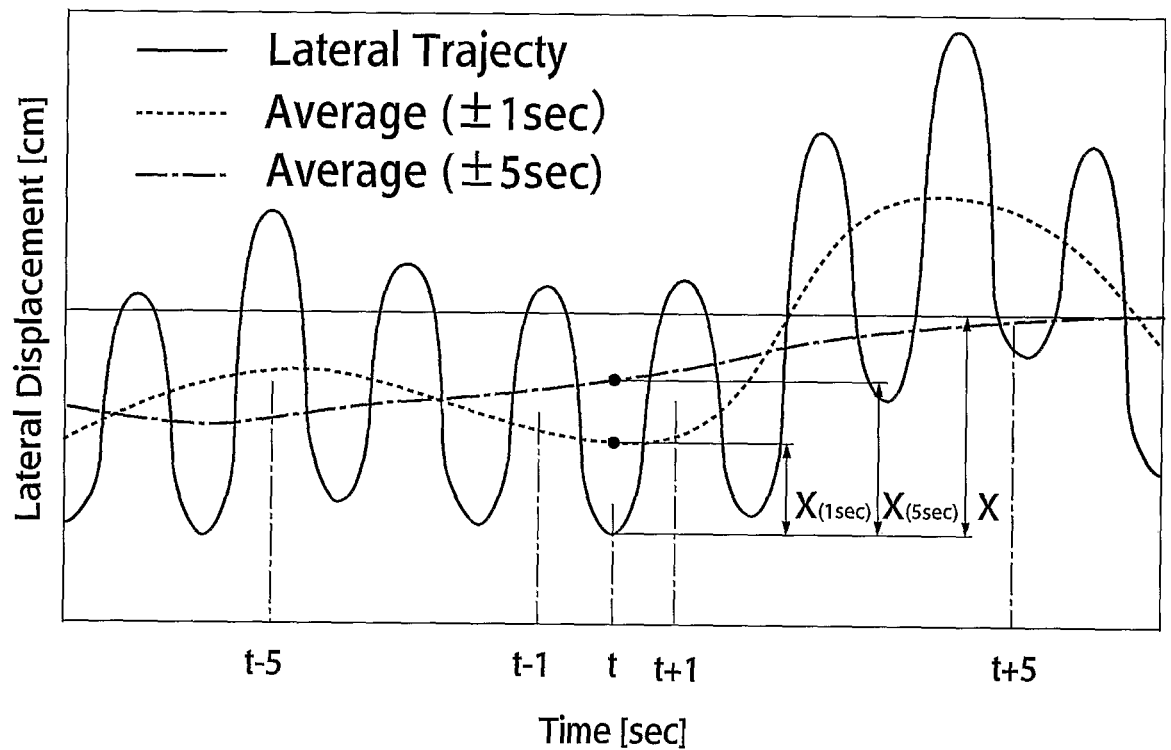
FIG. 10 shows calculation of displacements in the lateral direction.

FIG. 10 shows the results of calculated displacement in the left-right direction. The vertical axis represents the lateral displacement, and the horizontal axis represents time. There are shown the motion locus, the average $X_{1sec}$ for the short term (1 second each before and after the moment in question), and the average $X_{5sec}$ for the long term (5 seconds each before and after the moment in question).

For Advancing Direction: As for the advancing direction, first the speed V'z, with offset removed, is obtained by using the average speed Vz, like for the vertical and lateral direction. However, the method for obtaining the displacement Z in the advancing direction is different in some points from that for the vertical and lateral directions. With the method of equation (2) which eliminates constant speed component on the assumption of periodic motion, V'z becomes only the speed amplitude component during the walk. Therefore, a method of walk speed estimation is used as described below.

Because the speed amplitude and the walk speed may be approximated with a regression line, the walk speed V''z is obtained as shown with the equation (6) by adding the amplitude of V'z (V'zmax) multiplied by a constant á as an average walk speed for the short term to the speed amplitude component V'z. The motion distance Z is obtained by integrating again the V''z. The relationship between amplitude and speed varies from one individual to another. The value of a needs to be calculated and set for every individual from actual walk distance and time.

$$V''_z(t) = V'_z + \alpha V'_{zmax} \qquad (6)$$

Thus, the walk loci in three dimensions are obtained by the use of calculation method corresponding to the respective actions in three-dimensional directions.

Next, a method of evaluating the walk locus is described.

From the walk locus obtained through the above method, indices for understanding disability of every subject, and evaluating the walking aid apparatus are created. For that purpose, assuming application to a subject, a hemiplegic patient, characteristics of the hemiplegic patient's walk motion are listed.

Figure 11:
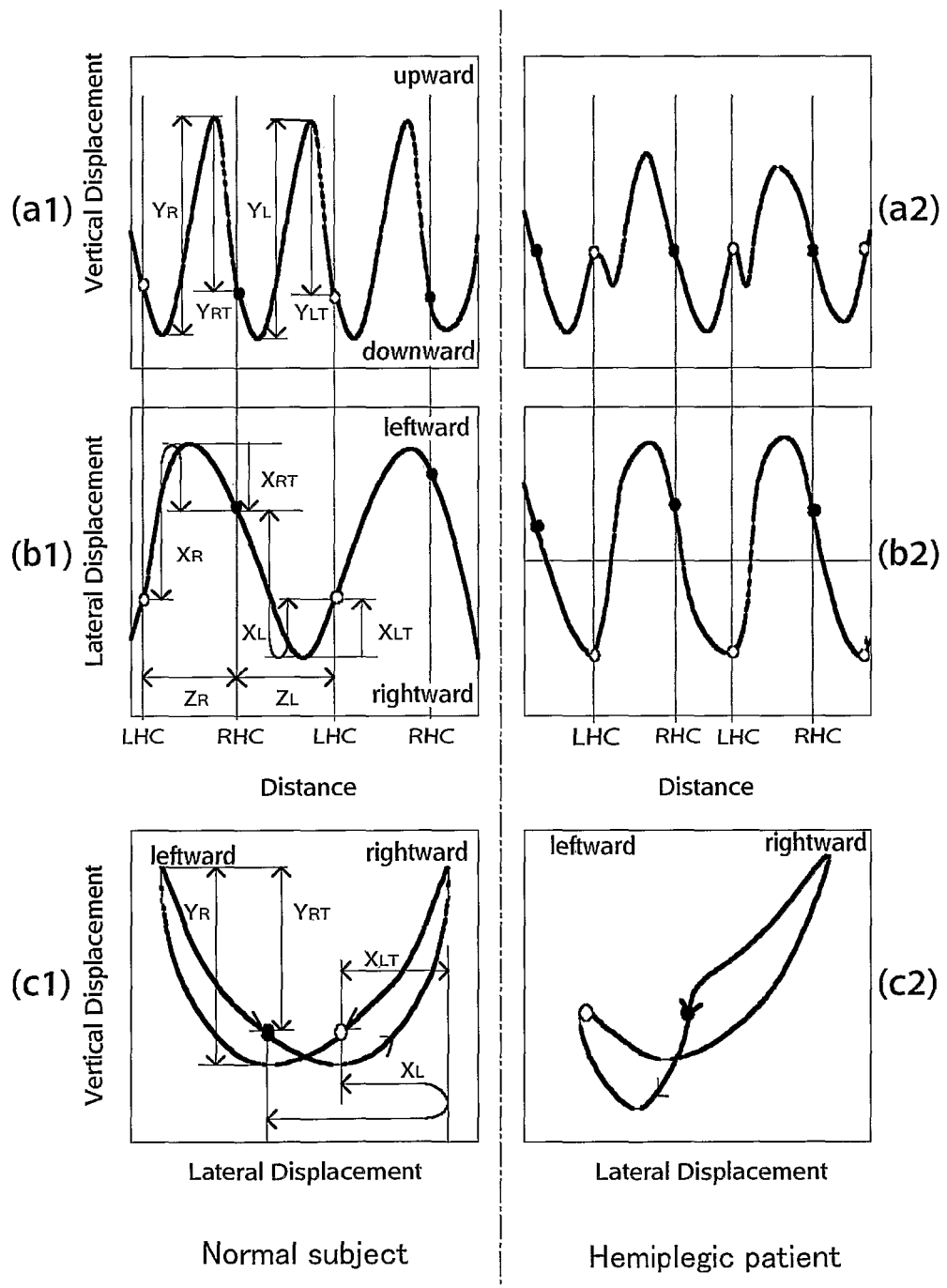
FIG. 11 shows examples of walk loci of the normal subject and the hemiplegic patient as compared with each other.

FIG. 11 shows examples of walk loci of a normal subject and a hemiplegic patient as compared with each other. FIG. 11 shows typical examples of them. Graphs on the left (FIGS. 11(a1)-(c1)) represent the normal subject, and on the right (FIGS. 11(a2)-(c2)), the hemiplegic patient. Motion direction combinations are shown from top to down: advance-vertical ((a1), (a2)), advance-lateral ((b1), (b2)), and lateral-vertical ((c1), (c2)). The symbol LHC (left heel contact) denotes the timing of left heel ground contact, and RHC (right heel contact), the timing of right heel ground contact. In order to evaluate these walk loci quantitatively, characteristic points on the loci are numerically expressed using indices.

$X_R$, $X_L$: rightward and leftward displacements.

$X'_R$, $X'_L$: ratio of step-back to displacement; ($X_{RT}/X_R$, $X_{LT}/X_L$).

Xa: asymmetry of left-right displacements; $(X_L/X_R-1)$.
$Y_R, Y_L$: vertical displacements.
$Y'_R, Y'_L$: ratio of torso lift to vertical amplitude $(Y_{RT}/Y_R, Y_{LT}/Y_L)$.
Ya: asymmetry of vertical displacements $(Y_L/Y_R-1)$.
Z, Za: step $(Z_L+Z_R)$ and its asymmetry $(Z_L/Z_R-1)$.
T, Ta: walk period $(T_L+T_R)$ and its asymmetry $(T_L/T_R-1)$ The above indices are used to understand the walk disability and evaluate the effectiveness of the apparatus.

Next, a measurement method for evaluating the effectiveness will be described.

Subjects were five males in their twenties of normal health, measured on the following conditions over a distance of straight 50 meters.

The subject walks at speeds the subject feels slow, normal, and fast, respectively.

The subject, assumed to be hemiplegic, walks with the right knee and ankle fixed.

The subject in the state of being assumed to be hemiplegic walks with the Walk-Mate.

By courtesy of three hemiplegic patients, clinical measurements were made under two kinds of conditions, free walk and walk with the Walk-Mate. Age, degree of paralysis, and walk ability of the three hemiplegic patients (A, B, and C) are shown in Table 3.

The walking aid system, Walk-Mate, senses, with an acceleration sensor attached to the ankle (waist in the embodiment), ground contact of the leg as the walk rhythm, which is in turn used entrainment phenomenon in mutual adaptation with the walk rhythm of the virtual robot in the computer, to carry out synchronized walk.

Next, measurement results will be described. First, calculation of the walk locus is described.

Figure 12:
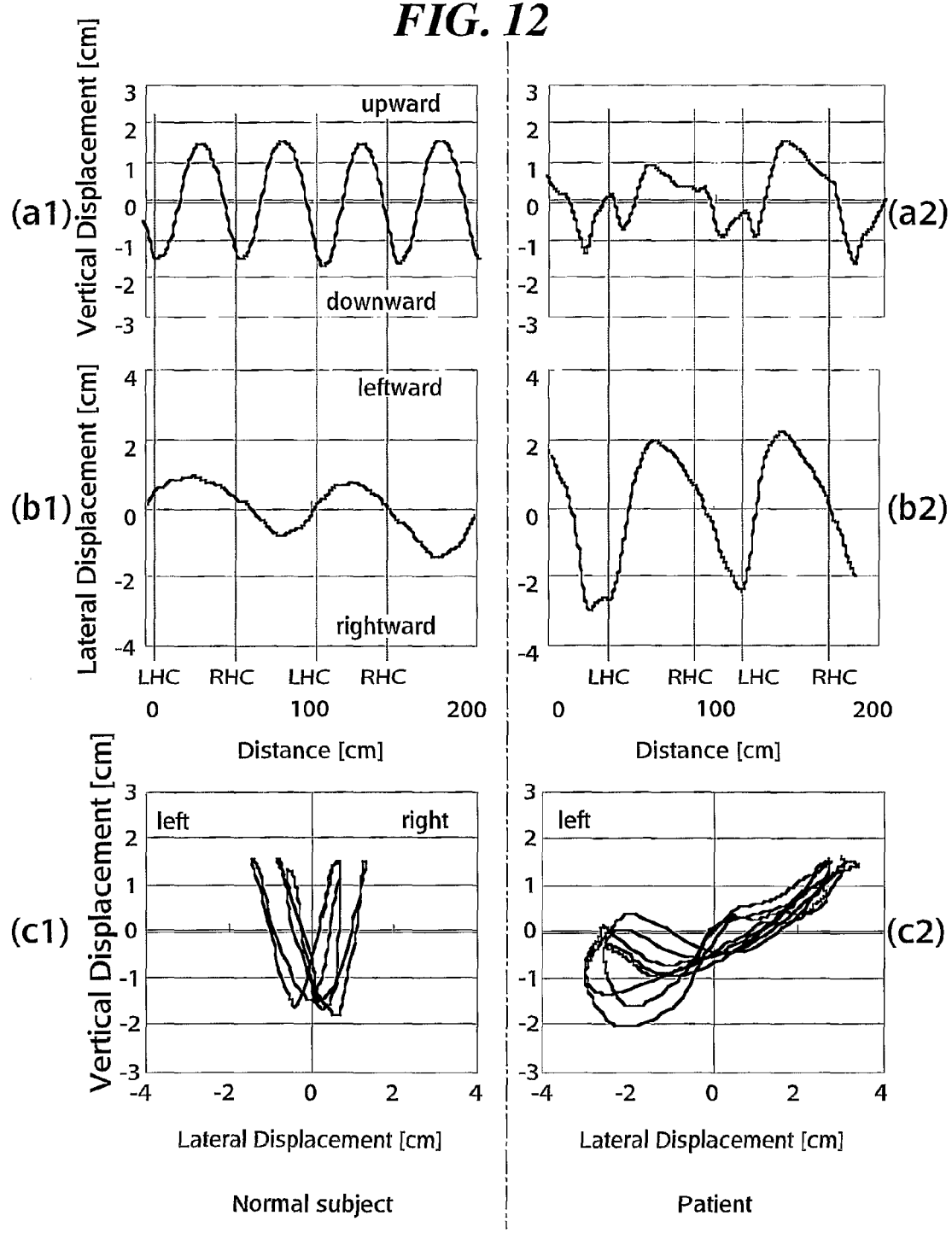
FIG. 12 shows examples of walk loci of the normal subject and the hemiplegic patient as compared with each other.

FIG. 12 shows an example of actual walk locus obtained by integrating the acceleration information obtained from measurements of walk of subjects. Graphs on the left (FIGS. 11(a1)-(c1)) represent the normal subject, and on the right (FIGS. 11(a2)-(c2)), the hemiplegic patient. Combinations are from top to down: advance-vertical ((a1), (a2)), advance-lateral ((b1), (b2)), and lateral-vertical ((c1), (c2)). From the walk analysis heretofore and the walk locus obtained here, it can be said that the normal subject walks in the following combinations from the left leg ground contact (LHC) to the right leg ground contact (RHC).

Vertical:
 Descent (Displacement of center of gravity).
 Ascent (Lifting free leg; Torso lift with support leg).
 Descent (Descent of free leg for ground contact).
Lateral:
 Displacement toward the support side (Displacement of center of gravity).
 Back to the free leg side (Displacement toward the next support leg).

When the walk of the normal subject is compared with the walk of the hemiplegic patient, differences are seen between the disabled free leg (from LHC to RHC) and the normal free leg (from RHC to LHC) in the lateral locus, vertical locus, and the footstep. These characteristics of the hemiplegic patient may be enumerated below.

Amplitude is great in lateral direction, small in vertical direction.

Free normal leg does not step back from end.

Torso does not lift in vertical direction of free normal leg.

From the walk loci obtained as described above for the normal subject and the hemiplegic patient, it is confirmed that they have greatly different characteristic points in torso behavior in the stage of visual observation of the loci.

Next, evaluation of the walk locus will be described. Table 4 shows the walk parameters obtained from the walk locus in the order of the normal subject, quasi-hemiplegic patient, and three hemiplegic subjects (A, B, and C). As seen from the lateral amplitude X in Table 4, the right side amplitude $X_R$ is 3.39±0.70 for the normal subject. In comparison with quasi-patient Q, and patient A, the same data for the quasi-patient is as great as 20.85±6.23, and for the patient A, as great as 6.77.

Here, the data values for lateral and vertical directions for the quasi-hemiplegic patient is greater than that for the patient A. This is because the expansion and pattern of motion of the hemiplegic patient are restricted by instability due to low tonus of muscles and reflective action due to spasmodic tonus. In contrast, because the quasi-hemiplegia patient is a disability made artificially by fixing joints, compensating actions are made by other members such as muscles and hip joint on the disabled side. Thus, a great difference occurs in amplitude between the two.

On the other hand, it has been reported heretofore that the lateral amplitude results in decrease in the walk, and the vertical amplitude, increase, along with the increase in speed. Therefore, evaluation by amplitude only is hard. Results of tests for confirming the above are shown in Table 5, in which the normal subject walked at three speeds the subject felt to be slow, normal, and fast.

Figure 13A:
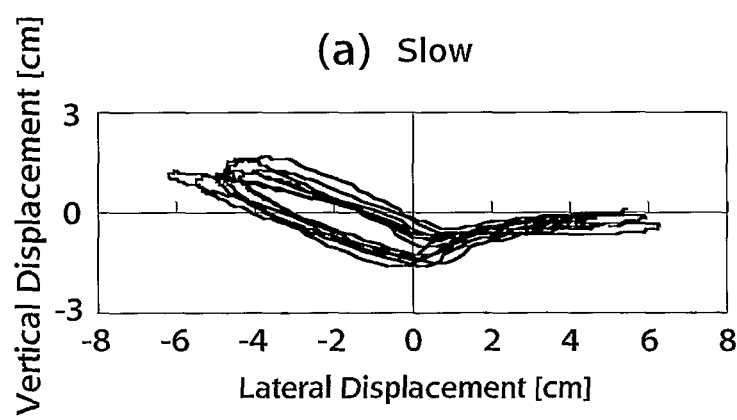
FIG. 13 shows an example of change with speed in the abdominal locus.
Figure 13B:
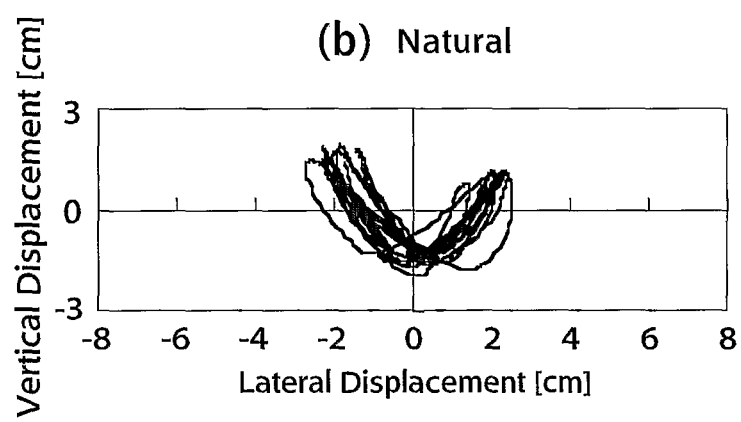
Figure 13C:
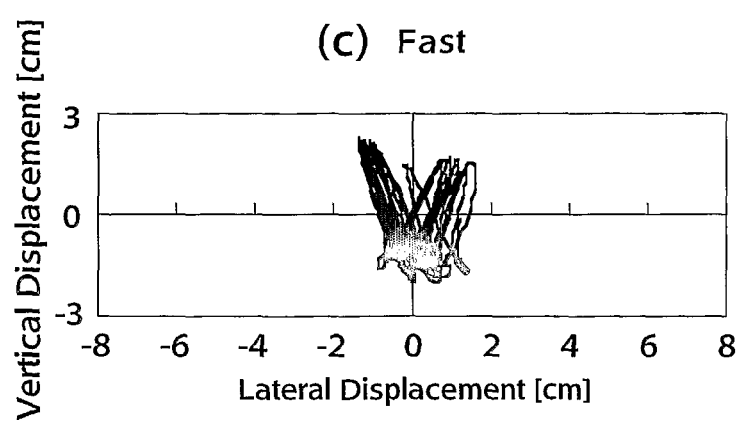
Figure 14A:
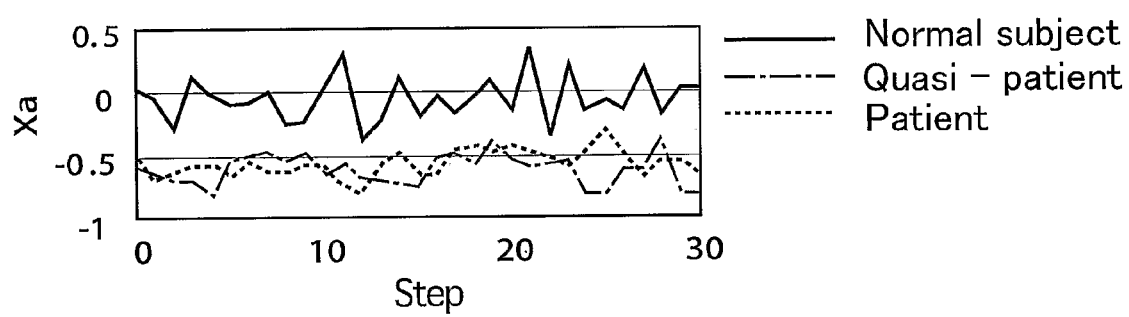
FIG. 14 shows an example of transition of the walk parameters.
Figure 14B:
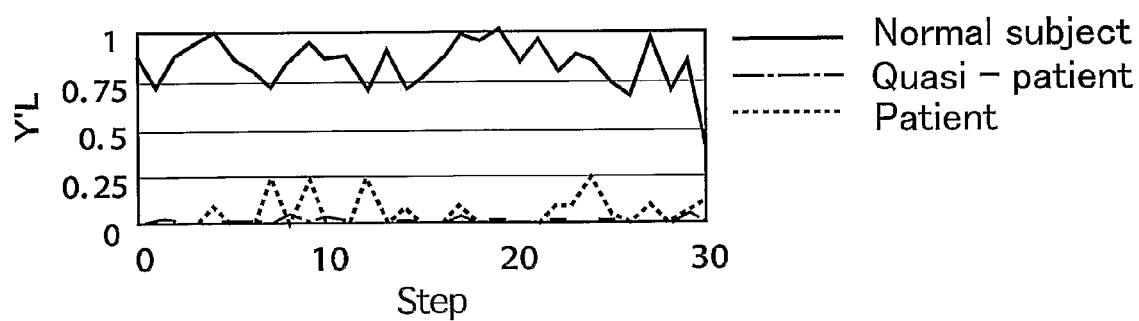
Figure 14C:
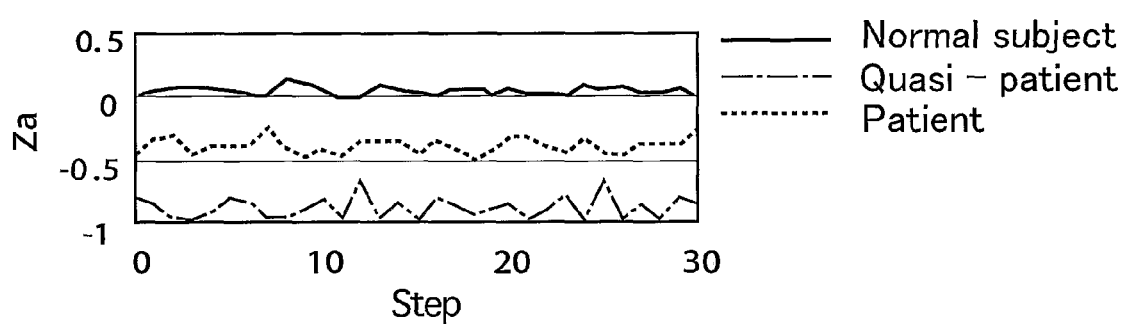
Figure 14D:
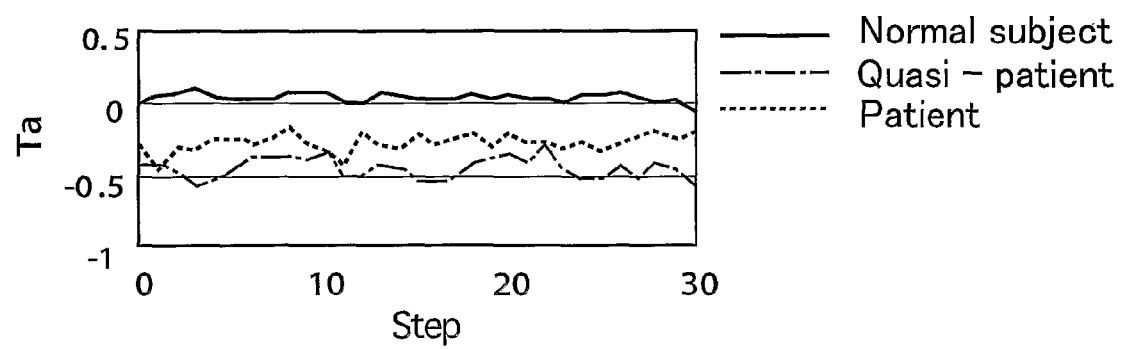
Figure 15A:
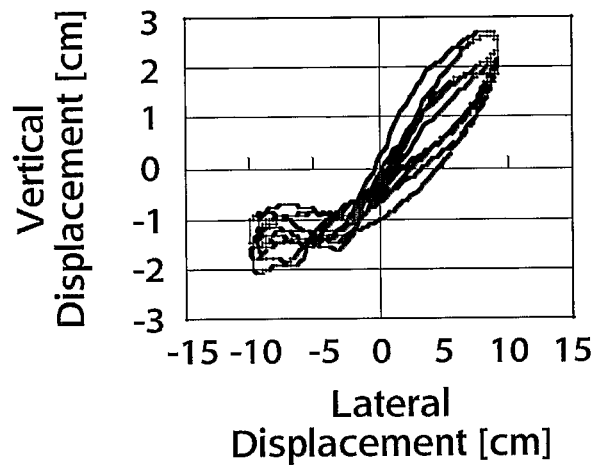
FIG. 15 shows an example of effect by the use of the walking aid system.
Figure 15B:
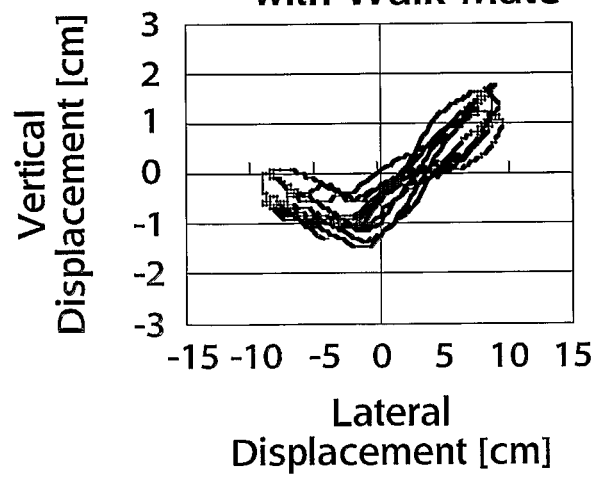
Figure 15C:
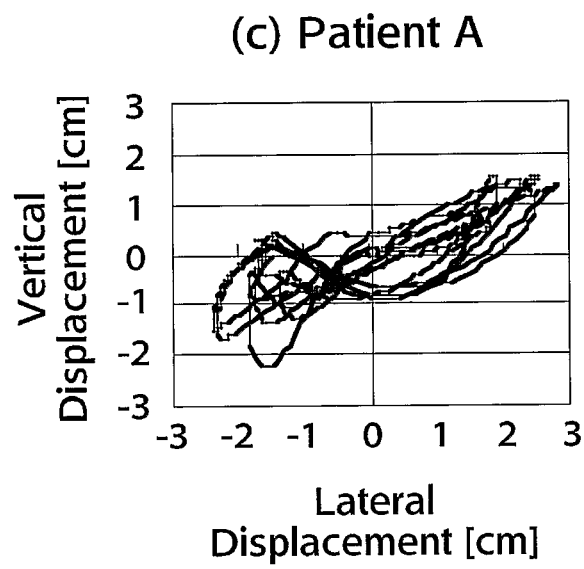
Figure 15D:
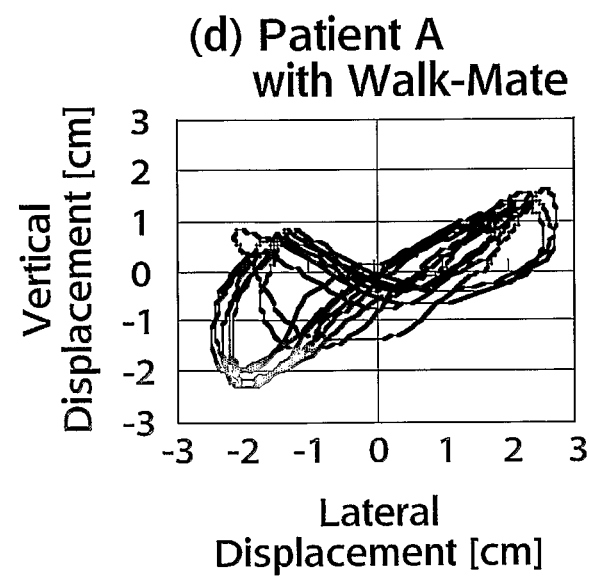

FIG. 13 shows an example of locus obtained by the above verification tests. Resultant loci of walk at speeds the walker felt to be slow (FIG. 13(a)), normal (FIG. 13(b)), and fast (FIG. 13(c)) are shown in that order from top. The acceleration sensor was attached to the abdomen. Therefore, the verification results are shown for the abdominal locus. As a result, tendencies were shown that, along with the increase in speed, average lateral amplitude $X_L$ decreased to 6.57, 3.29, and 2.00, and average vertical amplitude $Y_L$ increased to 1.25, 2.35, and 2.90. The same tendencies were seen for $X_R$ and $Y_R$. However, no changes were seen for the respective values of asymmetry (Xa, Ya, and Za) and torso lift amount ratio (Y').

From the above results, evaluation is not made directly from the amplitude and displacement but asymmetry (Xa, Ya, and Za) and step-back ratio to displacement ($X'_L, X'_R, Y'_L$, and $Y'_R$) are used as evaluation indices. When the values of $X'_L$ and $X'_R$, indices other than the asymmetry are small, there is a risk of falling toward the support leg. It is shown that the free leg moves in advance to prevent the fall. However, because the walk motion converts energy between potential energy and kinetic energy without waste by smoothly shifting the center of gravity, if the center of gravity remains on the support side, energy conversion for the succeeding action cannot be made smoothly. Further, smaller the values of $Y'_L$ and $Y'_R$ are, the less they show that the heel lift and leg stretching are made with the support leg. It shows that the walk is inefficient without smooth conversion between kinetic energy and potential energy.

FIG. 14 shows example transition of the cases when respective walk parameters as indices are compared with the normal subject N, quasi-patient Q, and patient A. Data shown are from top for: indices Xa (FIG. 14(a)), $Y'_L$ (FIG. 14(b)), Za (FIG. 14(c), Ta (FIG. 14(d)). Figures are extraction for 30 steps of walk.

As seen from Table 4, first, concerning the index Xa, the lateral asymmetry, as contrasted with an average value 0.04±0.01 for the normal subject N, other two are greater as −0.56±0.10 for the quasi-patient Q, and −0.55 for the patient A, when the disabled leg is free. This results from the compass walk with the torso tilted toward the healthy side, with the disabled side lifted. In the vertical direction too, because up and down motion is made not by lifting the disable leg but by tilting the torso, different subjects showed different average values of $Y'_R$ (not shown): as contrasted with the average value for the normal subject 0.90±0.07, quasi-patient showed 0.82±0.20 and the patient A 0.63. As for $Y'_L$ on the other hand, as contrasted with 0.94±0.04 for the normal subject N, both the quasi-patient and the patient A are almost zero. This is because a series of motion generation to produce a propelling force by lifting the heel along with advancement cannot be made on the disabled side with the support leg. Both are characteristics of the compass walk in the hemiplegic walk.

Concerning the patient B, the value of Xa, asymmetry, is −0.14, smaller than that, −0.55, of the patient A, and close to the Xa of the normal subject. This is because the decrease in the support capability on the disabled side is compensated by the use of a walking stick to increase with the increase in $X_L$ of the free leg on the normal side. However, from the fact that $X'_R$ and $X'_L$ are almost zero, it may be said that no shift of the center of gravity for moving on to the next motion is made and therefore the walk is inefficient concerning the lateral motion. Concerning $Y'_L$, the value for the patient A is 0.01 while the patient B has a different value of 0.67. This is because the walking stick assists the torso lift during the support period on the disabled side.

Concerning the patient C, the lateral asymmetry Xa is 0.03 and the vertical asymmetry Ya is −0.08, close to that for the normal subject. Based on this, it can be said that the walk rehabilitation improved the hemiplegia and enabled healthy walk. On the other hand, the torso lift ratios for both legs, $Y'_L$ is 0.42 and $Y'_R$ is 0.45, which are smaller than Y' for the normal subject. Here, that the patient C is in his seventies while the normal subject twenties must be taken into consideration. Thus, the results are thought to have resulted from the difference in motion capability due to difference in age.

The above comparison between the normal and hemiplegic subjects has proved that understanding of the walk disability and the evaluation of gait improvement by absolute evaluation are possible with the use of the indices created.

Next, effectiveness evaluation for the walking aid system Walk-Mate is described.

Changes in the walk parameters due to the use of Walk-Mate are shown in Table 6 in the order of the subjects, each in the order of average and change rate (%).

FIG. 15 shows examples of transition of walk loci of the quasi-patient Q and the patient A by the use of Walk-Mate. FIG. 15 shows data for lateral vs. vertical directions, in which the quasi-patient Q on the left (FIGS. 15(a) and (b)) and the patient A on the right (FIGS. 15(c) and (d)) are shown in lateral direction; and (a) and (c) before the use of the walking aid system, and (b) and (d) in use are shown in vertical direction. Evaluations by time series analysis reported so far are related to the alleviation of asymmetry of the walk period Ta. Improvements are seen by 65% for the quasi-patient Q, 13% by the patient A, and 14% by the patient B. As for the patient C, since lateral symmetry has been shown with the results in Table 4 before the use of Walk-Mate, no change was seen.

Next, evaluation for every subject using the indices shown in this embodiment is described. As for Xa, alleviation by 50% was seen for the quasi-patient Q, and 11% for the patient A. As for the step-back $X'_L$ of the healthy side free leg, it has increased by 15% for the quasi-patient Q, and by 32% for the patient A. Therefore, it can be said that transition to the next motion is made smoothly for the support period with the free leg on the disabled side. Improvement of the step asymmetry Za by 77% for the quasi-patient Q and by 34% for the patient A shows that the displacement Z, has increased for the normal side free leg. This is due to the increase in motion amount on the normal side resulting from the increase in supporting force on the disabled side. However, the quasi-patient Q and the patient A greatly differ from each other in the torso lift $Y'_L$ while the normal side leg is free, with the patient A remaining unchanged in $Y'_L$. This is difference in the paralyzed portion. Because the quasi-patient Q can make a greater number of motion patterns by the use of unfixed portions in comparison with the hemiplegic patient. As for the patient B, the footstep distance asymmetry Za was alleviated by 22%, from −0.43 to −0.33. However, no change is seen for the lateral asymmetry Xa, −0.01 before use and −0.06 in use. This is because lateral motion has been assisted by the use of the walking stick before the use of Walk-Mate. For $X'_R$ and $X'_L$, amounts of change were likewise in the range of 2 to 3%. As for the patient C, like the asymmetry of the walk period, no change is seen.

Thus, the degree of improvement by the use of Walk-Mate varies greatly with the differences in the condition and walking ability of the subjects. However, for the same subject, it has been verified that the effectiveness of Walk-Mate as a walking aid system can be evaluated by relative evaluation of changes in indices due to the use of the apparatus.

According to this embodiment, improvement effect on the walk motion by the use of the walking aid system using mutual adaptation can be evaluated. Further, this method can be applied not only to the walking aid system using mutual adaptation but also to the ordinary walking aid system. First, improvement effect for individual patients can be evaluated from time series data on evaluation indices related to the walk motion of individual patients. For example, hemiplegic walk can be evaluated by the lateral asymmetry of the walk motion. Further, if the walk period is chosen as the evaluation index, accelerated walk and cowering can be evaluated from the change with time in the evaluation index. Second, effect of using the system can be evaluated from the change in the evaluation index before and during the use of the walking aid system. In that case, it is possible to evaluate what setting results in increase in the effect by variously changing the target value. From the above, appropriate evaluation of the improvement effect of the walking aid system is expected. Since the analyses are processed using computers, evaluation in real time is possible.

This embodiment also provides an evaluation method for evaluating objectively the gait of the walker.

The present invention is not limited to the above embodiment but may employ various other configurations without departing from the gist of the invention, as a matter of course.

For example, while these embodiments use rhythm sound as rhythm stimulus, optical stimulus or or functional electric stimulus may also be used. The sensor for sensing motion rhythm may be attached to positions other than the ankle and waist. Further, not only the acceleration sensor but the pressure sensor, pedometer, etc. may be used. Further, sensors for sensing physiological information may be used to add physiological information such as pulse, respiration, and myoelectric potential to the target value. It is also possible to widen the scope of the walking aid system application utilizing the mutual adaptation using the evaluation indices as target values. Further, the walker to be aided is not limited to the walk-disabled and the aged but may be normal people for adjusting their walking speeds on slopes and infants in walk training.

INDUSTRIAL APPLICABILITY

The present invention is used for walk motion aid and rehabilitation aid for the aged and the physically handicapped.

TABLE 1

|   |   | S I | p | S II |
|---|---|---|---|---|
| (A) | Stepsound | 0.026 | | 0.027 |
|   |   |   | 0.48 |   |
| (B) | Metronome | 0.027 | | 0.03 |
|   |   |   | 0.27 |   |
| (C) | Entrainment | 0.027 | | 0.02 |
|   |   |   | 0.05以下 |   |
| (D) | Co-creation | 0.029 | | 0.018 |
|   |   |   | 001以下 |   |

TABLE 2

|   |   | S I | p | S II |
|---|---|---|---|---|
| (A) | Stepsound | −9.27 | | −9.07 |
|   |   |   | 0.12 |   |
| (B) | Metronome | −7.99 | | −7.75 |
|   |   |   | 0.11 |   |
| (C) | Entrainment | −923 | | −9.01 |
|   |   |   | 0.1 |   |
| (D) | Co-creation | −7.45 | | −3.82 |
|   |   |   | 001以下 |   |

TABLE 3

| Patient | Age | Degree of paralysis | Walk ability |
|---|---|---|---|
| A | 72 | II~III | Independent gait |
| B | 57 | III | With walking Stick |
| C | 74 | IV | Independent gait |

TABLE 4

|   | normal Ave ± SD | quasi-patient Ave ± SD | Patient A | Patient B | Patient C |
|---|---|---|---|---|---|
| Speed (cm/s) | 108.7 ± 20.9 | 79.4 ± 12.4 | 68.1 | 44.5 | 67.8 |
| T(sec) | 1.20 ± 0.05 | 1.37 ± 0.09 | 1.53 | 1.91 | 1.19 |
| XL(cm) | 3.54 ± 0.86 | 9.32 ± 3.04 | 3.02 | 6.21 | 3.94 |
| XR(cm) | 3.39 ± 0.70 | 20.85 ± 6.23 | 6.77 | 6.32 | 3.81 |
| YL(cm) | 2.30 ± 0.82 | 3.05 ± 0.61 | 2.22 | 2.24 | 2.54 |
| YR(cm) | 2.35 ± 0.88 | 4.04 ± 1.06 | 2.09 | 0.92 | 2.76 |
| Z(cm) | 109.6 ± 25.6 | 118.9 ± 22.9 | 103 | 74.6 | 80.02 |
| Ta | 0.01 ± 0.04 | −0.51 ± 0.17 | −0.26 | 0.15 | 0.03 |
| Xa | 0.04 ± 0.10 | −0.56 ± 0.10 | −0.55 | −0.14 | 0.03 |
| Ya | 0.01 ± 0.15 | −0.19 ± 0.32 | 0.06 | 1.32 | −0.08 |
| Za | 0.03 ± 0.03 | −0.53 ± 0.09 | −0.41 | −0.43 | 0.08 |
| X'L | 0.44 ± 0.15 | 0.53 ± 0.14 | 0.22 | 0.03 | 0.28 |
| X'R | 0.44 ± 0.15 | 0.52 ± 0.08 | 0.42 | 0.04 | 0.31 |
| Y'L | 0.94 ± 0.04 | 0.04 ± 0.03 | 0.01 | 0.67 | 0.42 |
| Y'R | 0.90 ± 0.07 | 0.82 ± 0.20 | 0.63 | 0.27 | 0.45 |

TABLE 5

|   | Slow Ave. ± SD | Natural Ave. ± SD | Maximal Ave. ± SD |
|---|---|---|---|
| Speed(cm/s) | 77.7 ± 9.3 | 108.7 ± 20.9 | 137.6 ± 8.5 |
| T(sec) | 1.63 ± 0.13 | 1.20 ± 0.05 | 1.11 ± 0.11 |
| XL(cm) | 6.57 ± 3.41 | 3.39 ± 0.70 | 2.00 ± 0.99 |
| XR(cm) | 6.92 ± 3.74 | 3.54 ± 0.86 | 1.88 ± 0.70 |
| YL(cm) | 1.25 ± 0.17 | 2.35 ± 0.88 | 2.90 ± 0.50 |
| YR(cm) | 1.38 ± 0.39 | 2.30 ± 0.83 | 2.98 ± 0.42 |
| Z(cm) | 123.4 ± 8.4 | 130.6 ± 32.3 | 139.2 ± 23.6 |
| Ta | 0.02 ± 0.02 | 0.01 ± 0.04 | 0.03 ± 0.02 |
| Xa | 0.04 ± 0.04 | 0.04 ± 0.11 | −0.01 ± 0.16 |
| Ya | 0.10 ± 0.21 | 0.01 ± 0.15 | 0.03 ± 0.03 |
| Za | 0.04 ± 0.02 | 0.03 ± 0.03 | 0.01 ± 0.01 |
| X'L | 0.39 ± 0.16 | 0.44 ± 0.15 | 0.62 ± 0.06 |
| X'R | 0.40 ± 0.16 | 0.45 ± 0.13 | 0.62 ± 0.07 |
| Y'L | 0.87 ± 0.22 | 0.90 ± 0.07 | 0.94 ± 0.04 |
| Y'R | 0.95 ± 0.01 | 0.94 ± 0.04 | 0.97 ± 0.05 |

TABLE 6

|   | quasi-patient | variation (%) | Patient A | variation (%) | Patient B | variation (%) | Patient C | variation (%) |
|---|---|---|---|---|---|---|---|---|
| T (sec) | 1.65 ± 0.24 | 11 | 1.51 | −2 | 1.89 | −1 | 1.09 | −9 |
| XL (cm) | 11.74 ± 2.41 | 26 | 3.33 | 10 | 5.29 | −15 | 4.49 | 14 |
| XR (cm) | 16.61 ± 5.41 | −21 | 6.61 | −2 | 5.60 | −11 | 4.96 | 30 |
| YL (cm) | 1.01 ± 0.39 | −61 | 2.95 | 33 | 1.44 | −36 | 2.69 | 6 |
| YR (cm) | 2.62 ± 0.03 | −35 | 1.92 | −8 | 0.94 | −3 | 3.40 | 23 |
| Z (cm) | 103.8 ± 29.7 | −9 | 93.77 | −9 | 69.29 | −7 | 68.65 | −14 |
| Ta | −0.19 ± 0.04 | −65 | −0.22 | −13 | 0.13 | −14 | 0.02 | 100 |
| Xa | −0.28 ± 0.11 | −50 | −0.49 | −11 | −0.06 | 286 | −0.09 | −385 |
| Ya | −0.61 ± 0.15 | 106 | 0.54 | 753 | 0.53 | −60 | −0.21 | 155 |
| Za | −0.11 ± 0.08 | −77 | −0.27 | −34 | −0.33 | −22 | 0.01 | −89 |
| X'L | 0.68 ± 0.16 | 15 | 0.28 | 6 | 0.01 | −2 | 0.23 | −5 |
| X'R | 0.65 ± 0.14 | 13 | 0.44 | 2 | 0.01 | −3 | 0.20 | −11 |
| Y'L | 0.31 ± 0.04 | 27 | 0.00 | −1 | 0.37 | −30 | 0.61 | 21 |
| Y'R | 0.87 ± 0.11 | 5 | 0.97 | 34 | 0.11 | −16 | 0.36 | −9 |

The invention claimed is:

1. A walking aid apparatus for controlling a motion rhythm of a walker as a controlled object having a characteristic of a nonlinear system comprising:
   a sensor section attached to the walker for sensing the motion rhythm of the walker;
   a main section including a nonlinear system module having dynamic behavior as a nonlinear system and for establishing a synchronized state through entrainment in interaction between the nonlinear system module and the walker, and further including a feedback system module for performing feedback to the nonlinear system module in the synchronized state; and a stimulus generating section for generating rhythm stimulus to the walker;

wherein the nonlinear system module generates a timing signal to establish the synchronized state with the motion rhythm of the walker through the entrainment and the rhythm stimulus is generated according to the timing signal and transmitted to the walker through the stimulus generating section, and the feedback system module, in the synchronized state of the nonlinear system model and the walker, calculates a relative amount for synchronizing, compares the relative amount for synchronizing with a relative amount as a target, calculates an appropriate feedback control amount, and applies feedback so as to adjust a parameter of the nonlinear system module for changing the relative amount for synchronizing to control the motion rhythm of the walker by causing the relative amount for synchronizing to converge to the target relative amount, wherein the relative amount for synchronizing is a phase difference between the motion rhythm of the walker and the rhythm of the rhythm stimulus, the relative amount as a target is a phase difference as a target between the motion rhythm of the walker and the rhythm of the rhythm stimulus, the feedback control amount is a control amount based on these two phase differences, and parameter for changing the synchronized state is a tempo or a phase of the timing signal generating a tempo of the rhythm stimulus or a phase of the rhythm stimulus.

2. The walking aid apparatus of claim 1, wherein the main section includes an input section for receiving the motion rhythm sensed with the sensing section as measurement, an interface section for functioning as human interface or network interface, a recording section for recording the measurement of the motion rhythm sensed with the sensor section, a target setting section for setting a target value for the motion information such as the motion rhythm of the walker, an operating section for calculating a walk rhythm, ground contact timing, walk distance or a walk speed based on the measurement of the motion rhythm sensed with the sensor section, a timing generating section for generating timing signals according to both the measurement and the target value, an output section for outputting the timing signal generated with the timing generating section to the stimulus generating section, and a control section for storing a control program for the walker and for controlling signals and data flow within or among the sensor section, the main section and the stimulus generating section;

the input section, the operating section, the timing generating section, the output section and the control section have the function of the nonlinear system module; and the target setting section has the function of the feedback system module.

3. The walking aid apparatus of claim 2;

wherein the control section has a control program for the walker which creates a virtual robot of a virtual space in a computer which synchronize with the walker in a real space so that the footstep sound of the walker as the motion rhythm sensed with the sensing section is transmitted to the virtual robot and the footstep sound of the virtual robot as the rhythm stimulus is returned to the walker.

4. The walking aid apparatus of claim 1;

wherein the motion rhythm is transmitted from the walker to the nonlinear system module through the sensor section, and the rhythm stimulus is transmitted from the nonlinear system module to the walker through the stimulus generating section; and the feedback system module, in the synchronized state, controls the motion rhythm of the walker by causing the relative amount for synchronizing to converge to the target relative amount, and realizes stabilization of the walk motion of the walker through the entrainment and the feedback.

5. The walking aid apparatus of claim 2;

wherein the sensor section has sensors on left and right feet of the walker respectively, each sensor measures motion rhythm of the left or right feet respectively, the target setting section is capable of setting target values for left and right rhythm stimuli respectively, the timing generating section generates timing signals related to left and right rhythm stimuli according to two sets of measurements and target values respectively, and the stimulus generating section generates rhythm stimuli to left and right ears or eyes according to the respective timing signals; and the nonlinear system establishes the synchronized state through the entrainment in interaction between the nonlinear system and left and right motion rhythm of the walker respectively, and the feedback system module performs feedback to the nonlinear system module in the synchronized state so as to control the left and right motion rhythm of the walker by causing left and right relative amount for synchronizing to converge to left and right target relative amount respectively.

6. The walking aid apparatus of claim 1;

wherein the sensor section has an acceleration sensor attached to an waist of the walker, an walk locus of the walker can be calculated from the acceleration information sensed with the acceleration sensor, the walk locus is obtained for the walk motion in vertical, left and right directions assuming that the walk motion is periodic oscillating motion by the alternation of both legs, an acceleration information is integrated to obtain a walk speed, an average value of the walk speed for short term having periodical deviation is obtained as baseline of the walk speed, displacement from the baseline of walk speed is obtained as an estimated speed, the estimated speed is integrated to obtain a walking position, the average value of the walking position is obtained as baseline of the walking position, and displacement from the baseline of the walking position is obtained as a locus, and the walk locus is obtained for the walk motion in advancing direction assuming that an average walk speed and an amplitude of walk speed may be approximated with a regression line, an acceleration information is integrated to obtain a walk speed, the walk speed removed offset is obtained by using a difference between the walk speed and an average walk speed for short term, an amplitude of the walk speed removed offset is multiplied by a constant to obtain an average walk speed for short term, the amplitude of the walk speed removed offset and the average walk speed for short term are added to obtain an estimated walk speed, and the motion distance is obtained by integrating the estimated walk speed.

7. The walking aid apparatus of claim 6;
the walk locus can be evaluated quantitatively using index such as rightward or leftward displacement, step-backs, ratio of step-backs to the rightward or leftward displacement, or asymmetry of left-right displacement for the walk motion in left and right direction, index such as vertical displacement, torso lift, ratio of torso lift to vertical amplitude, or asymmetry of vertical displacement for the walk motion in vertical direction, or index such as step, asymmetry of the step for the walk motion in advancing direction, walk period, asymmetry of walk period, fluctuation of walk period, asymmetry in ground contact or left-right fluctuation of the center of gravity of the body during a walk.

8. A gait evaluation apparatus for evaluating a gait of a walker, comprising:
a sensor section having an acceleration sensor for sensing a walk motion including a motion rhythm of the walker;
a recording section for recording the measurement of the walk motion sensed with the sensor section,
wherein the gait evaluation apparatus obtains a three dimension walk locus of a waist or an abdomen of the walker from the sensed motion sensed with the sensor section, and evaluates a gait of the walker based on an evaluation index related to the walk locus of the walker;
as for the walk motion in vertical, left and right directions, an acceleration information sensed with the sensor section is integrated to obtain a walk speed, an average value of the walk speed for short term having periodical deviation is obtained as baseline of the walk speed, displacement from the baseline of walk speed is obtained as an estimated speed, the estimated speed is integrated to obtain a walking position, the average value of the walking position is obtained as baseline of the walking position, and displacement from the baseline of the walking position is obtained as a locus, and
as for the walk motion in advancing direction, an acceleration information is integrated to obtain a walk speed, a walk speed removed offset is obtained by using difference between the walk speed and an average walk speed for short term, an amplitude of the walk speed removed offset is multiplied by a constant to obtain an average walk speed for short term, the amplitude of the walk speed removed offset and the average walk speed for short term are added to obtain an estimated speed, and a motion distance is obtained by integrating the estimated speed.

9. The gait evaluation apparatus of claim 8, wherein
the walk locus can be evaluated quantitatively using index such as rightward or leftward displacement, step-backs, ratio of step-backs to the rightward or leftward displacement, or asymmetry of left-right displacement for the walk motion in left and right direction, index such as vertical displacement, torso lift, ratio of torso lift to vertical amplitude, or asymmetry of vertical displacement for the walk notion in vertical direction, or index such as step, asymmetry of the step for the walk motion in advancing direction, walk period, asymmetry of walk period, fluctuation of walk period, asymmetry in ground contact or left-right fluctuation of the center of gravity of the body during a walk.

10. A gait evaluation method for evaluating a gait of a walker comprising:
sensing a walk motion including a motion rhythm of the walker with an acceleration sensor,
obtaining a three dimension walk locus of a waist or an abdomen of the walker from the sensed motion sensed with the sensor section, and
evaluating a gait of the walker based on an evaluation index related to the walk locus of the walker;
wherein, as for the walk motion in vertical, left and right directions, an acceleration information sensed with the sensor section is integrated to obtain a walk speed, an average value of the walk speed for short term having periodical deviation is obtained as baseline of the walk speed, displacement from the baseline of speed is obtained as an estimated speed, the estimated speed is integrated to obtain a walking position, the average value of the walking position is obtained as baseline of the walking position, and displacement from the baseline of the walking position is obtained as a locus, and
as for the walk motion in advancing direction, an acceleration information is integrated to obtain a walk speed, a walk speed removed offset is obtained by using difference between the walk speed and an average walk speed for short term, an amplitude of the walk speed removed offset is multiplied by a constant to obtain an average walk speed for short term, the amplitude of the walk speed removed offset and the average walk speed for short term are added to obtain an estimated speed, and a motion distance is obtained by integrating the estimated speed.

11. The gait evaluation method of claim 10, wherein
the walk locus can be evaluated quantitatively using index such as rightward or leftward displacement, step-backs, ratio of step-backs to the rightward or leftward displacement, or asymmetry of left-right displacement for the walk motion in left and right direction, index such as vertical displacement, torso lift, ratio of torso lift to vertical amplitude, or asymmetry of vertical displacement for the walk motion in vertical direction, or index such as step, asymmetry of the step for the walk motion in advancing direction, walk period, asymmetry of walk period, fluctuation of walk period, asymmetry in ground contact, left-right fluctuation of the center of gravity of the body during a walk.

* * * * *